United States Patent [19]

Mächler

[11] Patent Number: 5,680,209
[45] Date of Patent: Oct. 21, 1997

[54] SPECTROSCOPIC SYSTEMS FOR THE ANALYSIS OF SMALL AND VERY SMALL QUANTITIES OF SUBSTANCES

[76] Inventor: Meinrad Mächler, Sulzgasse 2, D-73479 Ellwangen, Germany

[21] Appl. No.: 381,911

[22] PCT Filed: Aug. 13, 1993

[86] PCT No.: PCT/EP93/02166

§ 371 Date: May 2, 1995

§ 102(e) Date: May 2, 1995

[87] PCT Pub. No.: WO94/04892

PCT Pub. Date: Mar. 3, 1994

[30] Foreign Application Priority Data

Aug. 13, 1992 [DE] Germany .................. 42 26 884.2
Mar. 15, 1993 [DE] Germany .................. 43 08 202.5

[51] Int. Cl.$^6$ ..................... G01J 3/02; G01J 3/42; G01J 3/447
[52] U.S. Cl. ..................... 356/319; 356/327; 356/328; 356/246; 250/373
[58] Field of Search ..................... 356/326, 328, 356/246, 410, 440, 319, 327; 250/573, 576, 373, 343, 339.13

[56] References Cited

U.S. PATENT DOCUMENTS 2,790,081  4/1957  Munday .................. 250/343

OTHER PUBLICATIONS

Stromberg et al, The Review of Scientific Instruments, vol. 41, No. 12, Dec. 1970, pp. 1880–1881.

*Primary Examiner*—F. L. Evans
*Attorney, Agent, or Firm*—Burns, Doane, Swecker & Mathis, L.L.P.

[57] ABSTRACT

A spectroscopic system for the analysis of small and very small quantities of substances makes use for the purposes of energy transfer of cone-shaped aperture changers (14, 15) which are arranged in the object zone (8) between the light source (L) and the sample (9) and, during absorption measurements, also between the sample (9) and the inlet slot (3) of a spectrometer (1). If the form used is a double cone, the aperture changers (14, 15) facilitate an oblique coupling in a capillary tube accepting the sample (9) which acts as a step-waveguide for the coupled radiation.

32 Claims, 18 Drawing Sheets

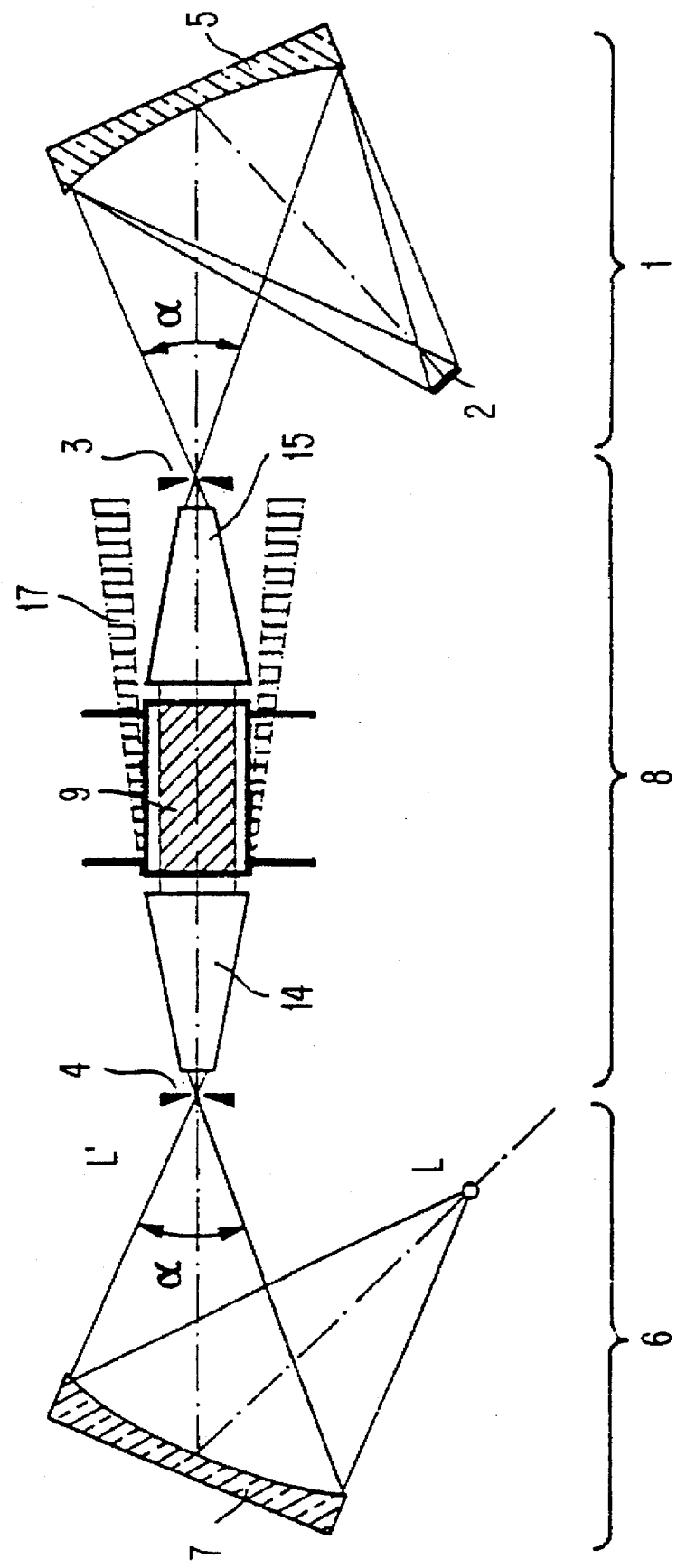

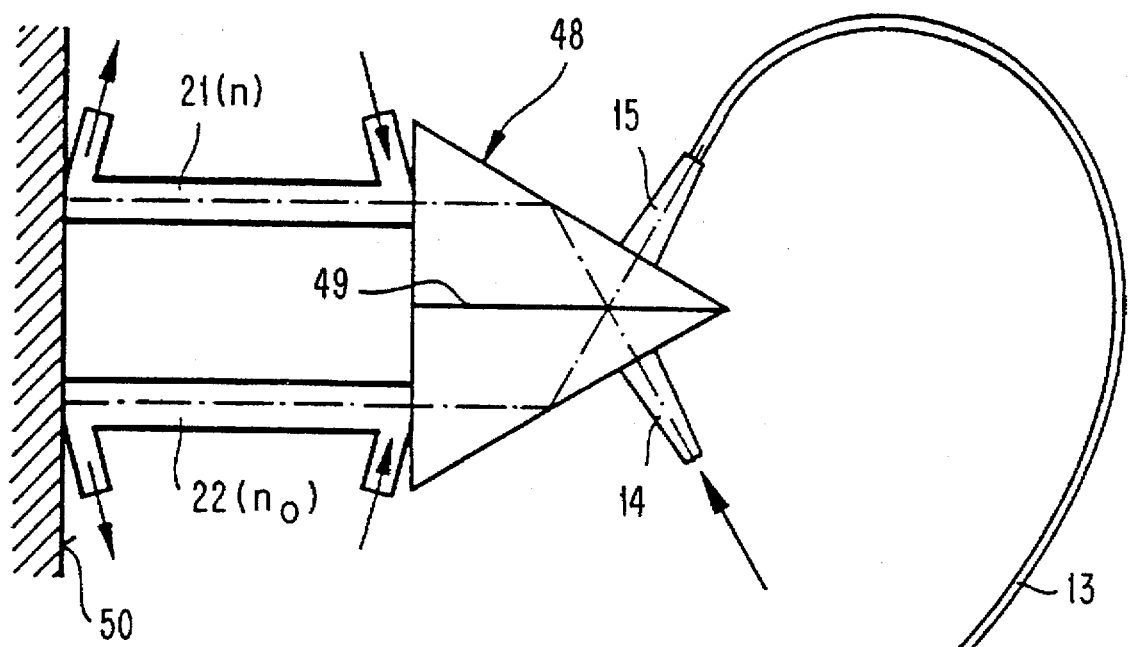
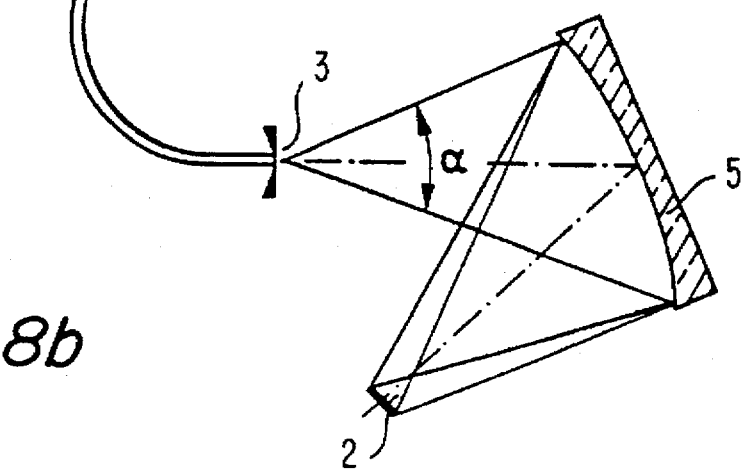
Fig. 8b

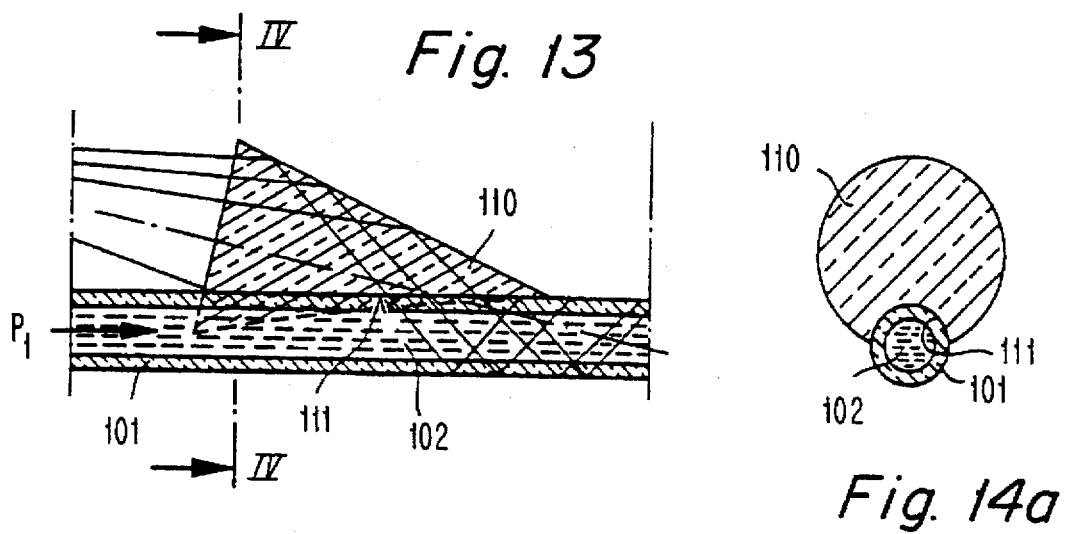
Fig. 13
Fig. 14a
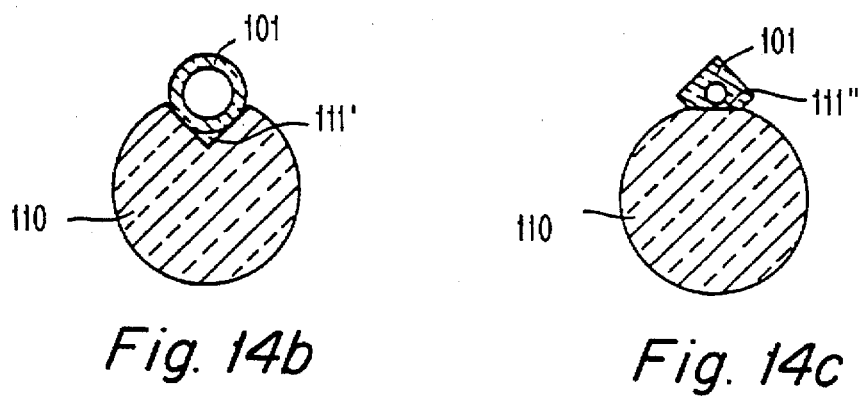
Fig. 14b
Fig. 14c
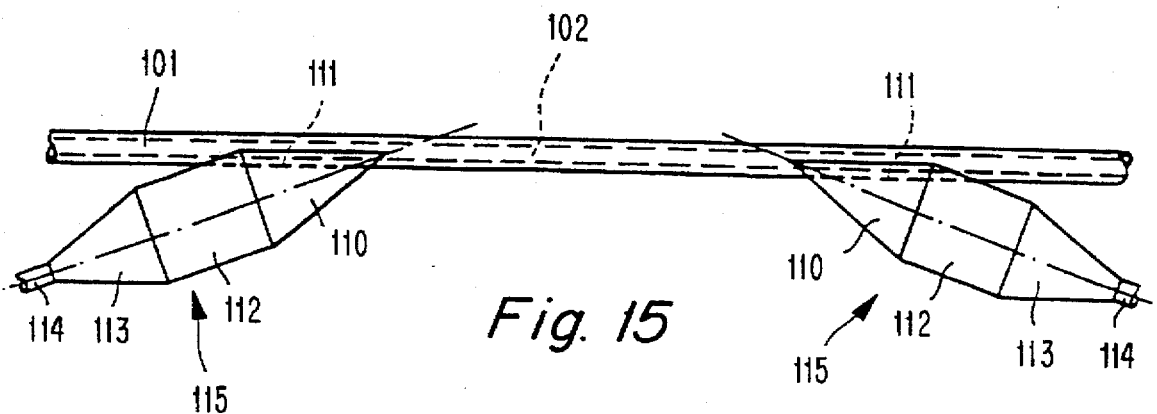
Fig. 15

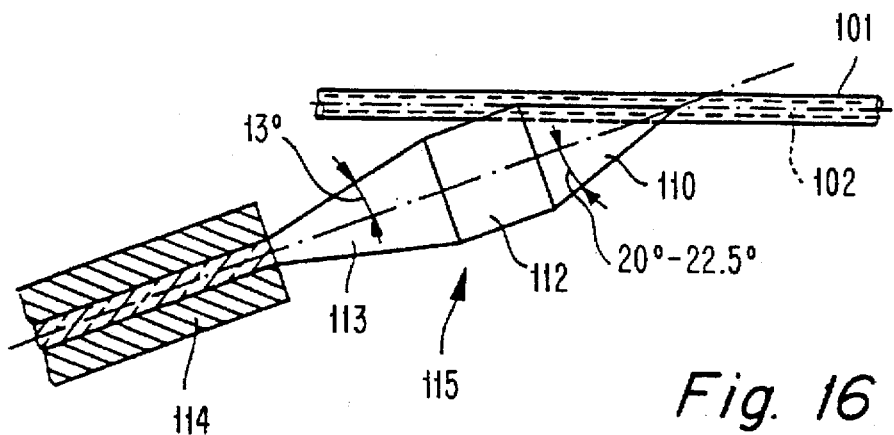
Fig. 16
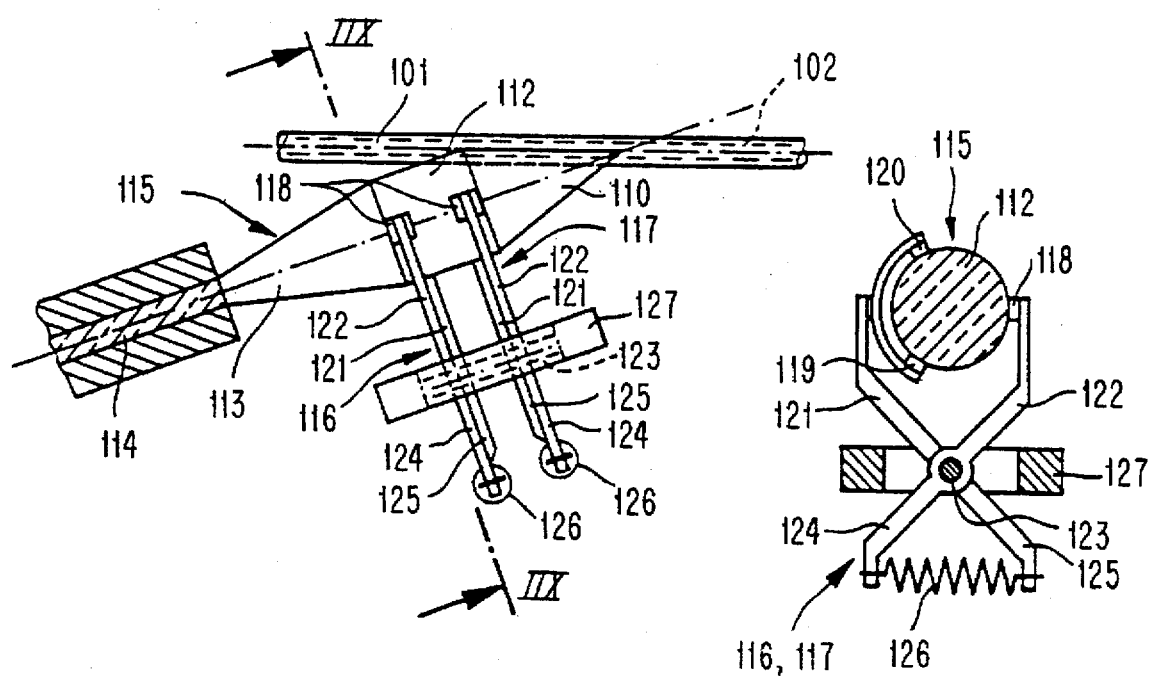
Fig. 17
Fig. 18

SPECTROSCOPIC SYSTEMS FOR THE ANALYSIS OF SMALL AND VERY SMALL QUANTITIES OF SUBSTANCES

DESCRIPTION

The invention relates to spectroscopic systems for the analysis of small and very small quantities of substance, particularly in the HPLC range.

Spectroscopic methods are frequently employed for analyzing substances in the fields of chemistry and biology.

Reference FR 2643147 A1 discloses a process and an apparatus for spectral photometry of liquids. Radiation vertically traverses the liquid to be tested in the direction of flow thereof by means of cone-shaped bodies. For this purpose, the large end faces of the cone-shaped bodies are directed at the liquid to be tested.

References DE-U-9013325 and GB-A 2116707 disclose optical systems for testing liquids, wherein the essential optical elements used for guiding the light are lenses.

None of the cited references are directed at a process for analyzing small and very small quantities of substance, however; nor do they refer to specific problems in micro-analytical procedures.

Reference U.S. Pat. No. 4,379,235 discloses the use of fiber-optical bundles in a scanner head for improving the spatial resolution of the scanner.

The inventive complex is directed to the analysis of very small quantities of substance. This automatically means that the sample spaces shrink to filament-shaped cylinders because of the largest possible path length. As there there can be no parallel irradiation, one has to rely on approximate solutions, preferred variants of which are described whithin the framework of this invention.

The simultaneous spectrometer developed by the applicant comprises a higher aperture than any other similar device and, as a result, achieves maximum energy efficiency and optimum spectral resolution. The high aperture entails one limitation: so-called "complete image formation" (in microscopy: Koehler's principle) is no longer possible with a lens system, as the spherical and chromatic errors limit the degree of transmission. (In microscopy, one can resort to immersion.) Hence, the solution resides in an aspherical mirror optical system.

FIG. 1 shows a prior art spectroscopy system wherein the spectrometer is a simultaneous spectrometer.

The core or main feature of the simultaneous spectrometer 1 is the use of self-scanning lines of diodes 2 which were developed by Snow in 1975 and comprise 512 single diodes over a length of 1.27 cm. The silicon diodes determine the effective spectral range of the simultaneous spectrometer 1 of about 200 to 1000 nm. The use of the lines of diodes 2 in a spectrometer as developed by the applicant is determined by the line geometry, a diode width of 25 µm defining the width of the exit slit 3 of the spectrometer. In the formation of images subject to the minimum error rate, i.e. 1:1, this is also the width of the entrance slit 3. The 12.52 mm spectrum length is extremely short for a spectrum of analytical interest, e.g. the visible range of from 400 to 800 nm, while the bandwidth of 0.8 nm is satisfactory. Said unusually small linear dispersion signifies a very short focal distance of the spectroscopic instrument, which would primarily result in a small dispersion element. The spectral resolution (Rayleigh criterion) for the 0.8 nm bandwidth cannot be realized in this manner, however, so that solutions based on prisms are ruled out. For a grating arrangement, short bandwidth, low groove density and large grating area, i.e. a small spectrograph having an extremely high relative aperture, are required. This automatically leads to a light conductance capable of competing with conventional instruments. The afore-said requirements of the grating 5 are met by holographically generated concave gratings.

A lighting unit 6 adapted to the design of the simultaneous spectrometer 1 is shown in FIG. 1. In order that the spectrometer 1 may be utilized with the highest efficiency possible, the arrangement is basically the same as in the spectrometer; an aspherical (ellipsoidal) mirror 7 having the same aperture replaces the high-aperture hologram grating 5. So as to achieve "complete image formation", i.e. the strictly conjugate sequence of source diaphragm—lens diaphragm, etc., the mirror 7 has the dimension of the grating 5. The light source L and the image L' of the light source which is the entrance diaphragm into the measuring device at the same time, have to be very small. The light source L is required to have a luminance as high as possible. This requirement is met by xenon lamps of minimum capacity (30 to 40 W) and an illuminated area of 0.3 to 0.5 mm, for instance. Deuterium lamps with illuminated areas of 0.5 mm, high luminance and a power consumption of 35 W are available for the ultraviolet range.

Between the diaphragm 4 with the light source image L' and the entrance slit 3 of the spectrometer 1 there is the object space 8 in which directional illumination, with only a slight inclination of rays against the optical axis, ideally: telecentric illumination, of an object or a sample 9 arranged in a sample cell is required.

To achieve this aim, an optical system comprising lenses 10, 11 used to be mounted in front of and behind the sample 9. In this manner, no significant energy efficiency is achieved, however; neither is it possible to restore the aperture required for achieving the spectral resolution (Rayleigh criterion) at the entrance slit 3 of the spectrometer 1. This means that the extraordinary possibilities offered by the simultaneous spectrometer 1 cannot be utilized in practice.

Attempts have therefore been made to solve the afore-said problem by using fiber-optical light guides 12, 13 in the object space 8, as shown in FIG. 2. Such light guides are also referred to as fiber-optical waveguides.

The fiber-optical light guides 12, 13 may be rigid or flexible monofibers or fiber bundles. Fiber-optical light guides are capable of transmitting the aperture concerned, α, of 30° or more in the ultrioviolet region and of up to 90° in the visible region without problem.

When the light is introduced in the fiber-optical light guide 12 at the location of the image L' of the light source, the light bundle leaves the light guide at the other end thereof having the same aperture and intensity distribution.

The fiber-optical light guide 12 is not capable of providing directional illumination of the sample 9 with an aperture smaller than the entrance aperture, however. In the optical sense, the exit aperture of the fiber-optical light guide 12 is a conjugate location with respect to the entrance area; however, even when there is a true optical image of the light source at the entrance, there is none at the exit, as each cross-section through the fiber-optical light guide is equivalent but not capable of forming an image. The exit area therefore has the optical effect of a hole. The light guide geometry, i.e. the aperture, is maintained, however. As the end of the fiber-optical light guide is not capable of forming an image, as mentioned before, it is not possible to generate a defined image on the basis of subsequent lens or mirror optical systems, either. One therefore has to put up with the fact that the problem of reversible aperture change cannot be solved by the combination of fiber-optical light guides with conventional lens or mirror systems, although various attempts have been made in this respect to no avail.

It is an object of the present invention to provide a spectroscopic system capable of achieving directional illumination of the sample together with optimum energy transmission. This object is solved according to the invention in that for the optical energy transmission in the object space between the light source or the image thereof and the sample as well as between the sample and the entrance slit there is provided a respective aperture changer which consists of a coaxial conical fiber-optical light guide or mirror having a light entrance opening and a light exit opening, the larger opening facing the sample, and the sample being contained in a capillary cell arranged between the aperture changers along the optical axis such that it is transilluminated substantially in the longitudinal direction.

The light entrance opening and the light exit opening of the aperture changer are preferably cross-sectional openings normal to the optical axis.

The spectrometer has a high aperture but extremely small slit and detector areas. The sample space requires a small aperture in connection with a small cross-sectional area. From the reciprocity: small area=large aperture, and large area=small aperture, it follows that, if the area of the spectrometer slit is considerably smaller than the cross-section of the sample, the requirement can be met with an aperture changer.

The spectroscopic system is preferably designed such that the totally reflecting periphery of each cone of each aperture changer is enclosed by a hermetically sealed hollow space whose walls are preferably made of the same material as the cones themselves, the hollow space conveniently being formed of a mounting cylinder in which the cone has been inserted. All fiber-optical light guides, i.e. also the aperture changers, are only capable of radiating divergent light pencils. If such energy loss in the marginal zones is to be prevented, e.g. because the stray light may have a disturbing effect, a correction lens may be additionally provided at the aperture changer, preferably at the larger cross-sectional opening thereof. As the aperture is already reduced at this location, a lens can be used. Like the preceding configuration, this embodiment preferably is a hermetically sealed, monolithic functional unit.

According to a preferred embodiment of the invention, at least a portion of a preferably cylindrical fiber-optical light guide is provided before the smaller cross-sectional opening of the aperture changer, the cross-section of said light guide corresponding to said smaller cross-section of the aperture changer preferably in the area of contact therewith, for coupling the aperture changer to the light source or the image thereof or the entrance slit of the spectrometer. The fiber-optical light guide is designed, at least between the end portions thereof, as a preferably flexible fiber-optical light wire.

The invention is based on the finding that in spectral analysis only problems regarding energy and optics (frequency, amplitude, velocity, azimuth and axial ratio of the electromagnetic radiation) have to be solved so that all questions regarding image position, image definition, etc. can be deferred, and the only important requirement is to guide the light or radiation through the object space with as little loss as possible and to adjust the inclination of rays, i.e. the apertures, to the measuring method by suitable means.

Refraction and diffraction effects are subject to dispersion, i.e. they are not achromatic, so that means based thereon have to be ruled out. The remaining means of choice therefore are reflection means; preferably, use is made of total reflection which is utilized in the fiber-optical light guides anyway.

The solution according to the invention can also be understood as the consequent reduction of a coaxial telescope with inner wall reflections on a very small funnel-shaped or cone-shaped aperture changer. The aperture changer can easily be coupled to the fiber-optical light guides which are used in many embodiments of the spectroscopic system anyway. As can be easily seen, the cone-shaped configuration of the aperture changer changes the aperture of the transmitted light such that the aperture is large at the small cross-section and small at the large cross-section.

According to another modification of the invention, a portion of a preferably cylindrical fiber-optical light guide is connected before the larger cross-sectional opening of the aperture changer, the cross-section of the light guide corresponding to said larger cross-sectional opening of the aperture changer in the region of contact therewith, for coupling the aperture changer to the sample, e.g. by means of cementing.

As regards the energy transport in the object space it is particularly useful for the end of a cylindrical fiber-optical light guide connected before the respective end of the aperture changer to be made of the same material as the aperture changer. This applies also to a lens that may be connected to an end of the aperture changer.

The respective fiber-optical light guide can be designed as a monofiber, a light-conducting rod or an optical fiber bundle; in the latter case, the fiber bundle adjacent the entrance slit of the spectrometer may be in the form of a slit in said end region, which slit replaces a separate entrance slit of the spectrometer. Besides, it has proven to be advantageous to choose the half cone angle β of the aperture changer such that a slight inclination of rays with respect to the optical axis is achieved when the object is illuminated.

The half cone angle of the aperture changer is smaller or equal to half of the maximum light exit angle from the fiber-optical light guide leading from the light source or the image thereof to the aperture changer disposed between the light source or the image thereof and the sample. As mentioned before, the light exit angle of said fiber-optical light guide is defined by the aperture of the lighting system, as the light-conducting geometry, i.e. the aperture, is maintained in the fiber-optical light guide.

If the system is intended for UV spectroscopy, quartz funnels are used as aperture changers; the fiber-optical light guides which are optionally connected therebefore, the enclosure forming the hollow space for receiving the aperture changer, and optionally a lens connected to the aperture changer are preferably made of quartz, too. With such a preferred configuration and an aperture of illumination of $\alpha=26°$, the half cone angle of the aperture changer $\beta \leq 6.5°$ and preferably is 5.5°.

According to another preferred embodiment of the system according to the invention, the illumination arrangement is a point or quasi point source of light which is imaged by an aspherical mirror, preferably an ellipsoidal mirror, on the entrance opening of the aperture changer disposed between the light source and the object or of the fiber-optical light guide connected before the aperture changer.

In the system according to the invention, the spectrometer preferably is an arrangement consisting of a diffraction grating and a receiving unit, the diffraction grating preferably being a holographic concave grating and the receiver being a line of photodiodes.

As a particular advantage, the mirror of the illumination device and the concave grating of the spectrometer have the same aperture and/or the light source is imaged 1:1 on the diodes of the photodiode line.

According to a preferred application of the system of the invention, the measuring cell disposed in the object space is provided such that one aperture changer each is connected, at the larger cross-sectional opening thereof, to the inlet and outlet of said cell directly or, optionally based on the kind of use, via beam splitters or analyzer and polarizer arrangements.

The at least one sample cell is advantageously designed as a flow-through cell.

In another preferred application of the system according to the invention, the object is a surface whose spectral reflectivity is measured. The surface can be illuminated substantially vertically, e.g. for optical stress measurements, or at an angle. In the latter case, the angle of incidence and the angle of reflection may be identical or may differ from each other along the lines of a gonio-spectrophotometer.

According to another preferred application of the system of the invention, an interferometer arrangement, e.g. in the form of a Michelson interferometer, a Jamin interferometer or a Mach-Zehnder interferometer, is provided in the object space. Conveniently, a measuring cell and a reference cell are provided.

An improvement of the system according to the invention employing an interferometer arrangement permits the dispersion of substances to be measured in a particularly elegant manner. Measuring the velocity of light in a homogenous matter, i.e. the refractive index, has been neglected in analytical processes in favour of absorption measurements so far, although absorption as imaginary part of the—always—complex refractive index is basically not more informative than the real part, the rate of propagation. However, absorption as a pure quantity of energy was more readily accessible metrologically. In the case of substances having resonant frequencies of the chemical bond beyond the accessible spectral range, however, the imaginary part disappears while the real part is maintained. This applies to a large number of hydrocarbons, including all sugars and alcohols, for instance.

The direct measurement of the refractive index usually is a measurement of angle, and in analytical procedures it is impaired by the fact that the analytically uninteresting solvent makes up the major portion of the resultant refractive index. In order to avoid this drawback, the invention suggests a differential-interferometrical measurement of the dispersion over the whole spectrum, said dispersion being obtained from the difference $n(\lambda)-n_0(\lambda)$, wherein $n(\lambda)$ designates the refractive index of the solution and $n_0(\lambda)$ designates the refractive index of the solvent. This method is superior to the pure dispersion spectra with respect to the accuracy of determination; besides, the applicant takes the view that there are no useful dispersion spectrometers available anyway.

In order to solve the above-mentioned object, the afore-described system which includes an interferometer arrangement is provided with at least one beam splitter for feeding the measuring light supplied by the inlet aperture changer to the inlets of the measuring cell and the reference cell and for supplying the light reflected at the opposite end of the cells after another passage therethrough to the outlet aperture changer. The substance which is dissolved in the solvent and the dispersion of which shall be investigated is preferably introduced in the measuring cell while the solvent is introduced in the reference cell.

By using a source of white light, and on the basis of the identical path lengths in the optical system for both paths of rays, interference patterns representative of the dispersion of the dissolved substance are obtained in the receiving plane of the spectrometer from the light collected in the outlet aperture changer in this manner. The interference patterns exhibit a periodic sequence of bright and dark portions in the receiving plane of the spectrometer, from which the refractive index with regard to the respective wavelength or the wavelength-dependent course of refractive index over the whole spectrum and thus the dispersion of the substance can be determined on the basis of the departure from linearity, i.e. from the change in the respective spatial frequency, e.g. via Fourier analysis. The significant advantage of this system resides in the fact that the whole dispersion of the substance to be investigated can be determined by one measurement when a simultaneous spectrometer is used.

According to another, particularly preferred application of the system according to the invention, a polarizing device is provided before the sample to be tested and an analyzing device is provided behind the sample to be tested—seen in the direction of the illuminating beam—for conducting polarization spectroscopy, wherein a spectrometer is connected to the analyzing device via a respective aperture changer for determining the rotary dispersion and the absorption spectrum of the sample on the basis of the photocurrents from the spectrometers.

Using the system according to the invention as a spectropolarimeter and absorption spectrometer in this manner is particularly interesting because it permits the combination of two totally different determinations on the basis of a single measurement, and what is more, as a spectral function. This metrological achievement also solves an urgent chemical-pharmaceutical problem, namely that of direct purity control in the separation of enantiomers.

In another preferred embodiment, the spectroscopic system according to the invention provides a possible way of measuring the circular dichroism (CD).

For this purpose, the system comprises a beam splitter which splits the light supplied by the inlet aperture changer in two paths of rays which are polarized orthogonally to each other during the splitting process, e.g. by means of a Glan prism, or thereafter. One of the orthogonally polarized bundles of rays is subsequently directed through a left-hand circular polarizer, the other through a right-hand circular polarizer, which polarizers can also be referred to as phase retardation members. The bundles of rays then traverse at least one measuring cell containing the substance to be tested. The two bundles of rays separately emerging from the measuring cell are subsequently supplied to respective spectrometers, preferably a simultaneous spectrometer, via respective aperture changers. As in the above-described optical rotary dispersion, the measured quantity is the difference or the sum of the photocurrents of the two spectrometers, the difference representing the circular dichroism, the sum representing the absorption spectrum.

As far as the afore-described spectroscopic systems are used for absorption spectroscopy, standard microcells, e.g. of HPLC, are generally employed. In ordinary absorption measurements, coaxial beams, path lengths in the cm-range and below in the case of flow-through cells, beam diameters of a maximum of 1 mm and typical cell volumes of 5 to 10 μl are standardized features, too.

It is another object of the present invention to use the spectroscopic system according to the invention also in connection with extremely small quantities of substance. Photometric (amplitude) measurements require certain minimum path lengths. The minimum volume for correct optical beam guidance is about 5 μl, as mentioned before. The desired further reduction of sample quantities has led to various types of instruments which are not very useful, however. A common feature inevitably is that the measurement is conducted in a capillary.

The further configuration of the invention described below for solving said problem is based on the following considerations.

The quantitative photometric analysis of liquids is based on the law of Bouguer-Lambert-Beer which refers to the relation of concentration-extinction and transilluminated path length as a spectral function.

As a precondition for the applicability thereof it is referred to the unhindered, i.e. non-reflecting, transillumination of the liquid with approximately parallel light. This automatically results in limited "light conductance" ("geometric flow" according to DIN) which gets lower in proportion to a reduction in the beam cross-section and an increase in the path length traversed, which is the case when small quantities of substance are to be subjected to measurements of high sensitivity, i.e. exclusively in microanalytical procedures. There have been repeated attempts to reduce the errors caused by reflections which inevitably occur at the inner walls of the cells by so-called "refractive index compensation". Such errors cannot be eliminated completely, however, as the dispersion of the cell material may be known but not the dispersion of the sample material. For this reason, the residual errors inherent in the system are reduced by permanent reference measurements, usually based on the solvent used, on the supposition that solution and solvent do not differ significantly with respect to refractive index and dispersion.

The present improvement of the invention was triggered by developments and findings in the spectral analysis of small quantities of substance as they are typical in the field of biochemistry, for instance. The absolute amounts of substance available are very often extremely small, e.g. in the case of glandular secretions, etc. The physiologically relevant concentrations are usually also very low so that it is often difficult, even impossible, to realize the path length required for a significant photometric effect, since infinitely small cell cross-sections cannot be irradiated with the required power density without reflection over major distances, as mentioned before.

For this reason, the present invention is based on the further object of providing a microcell system for use in absorption photometry, which ensures that the sample is irradiated with sufficient power density in spite of minimum cell cross-sections.

This object is solved according to the invention by a microcell system for absorption photometry which comprises a cylindrical cell tube having a hollow core for receiving a sample liquid which can be traversed at least in a longitudinal section of the hollow core by radiation whose absorption is subsequently measured, and which is characterized in that the cell tube and the sample liquid are adjusted with respect to the refractive index such that they act as a step waveguide for radiation, where the sample liquid forms the core and the wall of the cell tube forms the sheath so that radiation undergoes multiple reflection, preferably multiple total reflection, at the outside wall of the cell tube and the sample liquid is traversed by radiation several times.

Optimum radiation efficiency is achieved when radiation can be supplied to the step waveguide formed of cell tube and sample liquid at an aperture angle which corresponds to the maximum aperture of the step waveguide. The cell tube is preferably made of an isotropic material which is non-absorbing in the spectral range concerned.

The cell tube is advantageously designed as a circular cylindrical micro-capillary having an inside diameter of less than 0.5 mm, preferably less than 0.25 mm, more preferably less than 0.15 mm, and an outside diameter of less than 1.0 mm, preferably less than 0.35 mm, and more preferably less than 0.20 mm, so that sample liquids in the nanoliter range are sufficient.

The invention provides a longitudinally irradiated cell of measurable length which represents a light guide in principle. The measuring space is constituted by the liquid in the cylindrical core of the capillary. Guidance of the light beam (of any length) along the cell is effected by the non-absorbing coating or sheath of the capillary which always focusses the progressive bundle of rays on the centrically arranged sample space via total reflection.

The invention is based on the following simple principle: the cell walls, which are non-absorbing in the spectral range concerned, are integrated in the beam guiding system so that a step index waveguide is generated wherein the sample liquid is the core of the light guide and the cell walls are the sheath.

The reflections at the outer cell wall are loss-free total reflections. Analogous to an Ulbricht globe photometer, however of elongate shape, the light guide cell according to the invention is an integrator over the whole radiant flux along the entire length, i.e. light conductance as the product of aperture and entrance cross-section remains constant irrespective of the length and is higher by several orders of magnitude than in conventional cells.

However, the effective photometric path length, which is a function of the lengths of the traversed paths in the sample and the wall as well as the entrance aperture, has to be redefined. When the aperture and the distribution of radiation over the solid angle are known, the effective path length can be calculated for every specific microcell system. Investigations conducted by the applicant have shown, however, that usually minimum volumes are wrongly assessed to a large degree in photometric measurements. For the applicability of the photometric laws (Bouguer-Lambert-Beer, etc.) presupposes a geometric optical system without diffraction limitation the conditions of which are not fulfilled by today's micro and submicro methods, especially those according to the invention, however. The result is an inhomogenous distribution of energy in the space or in the direction of propagation (caused by interference and diffraction effects) which almost always goes unnoticed. Such energy discontinuities are compensated by the integrating effect of the light guide according to the invention so that correct photometric measurements are made possible. Due to the complexity of the theoretical calculation, however, calibration with standard substances is to be recommended. In practice, the effective path length is therefore determined on the basis of a reference measurement with a standard sample having the same geometric configuration and the same solvent.

The physical and analytical-methodical gains attained by the present invention concern the following crucial points:

1) Light conductance, i.e. the transferable optical intensity, and thus the photometric sensitivity correspond to the theoretically possible limit irrespective of the path length.

2) The cell, which can shrink to the dimensions of a capillary, exhibits the required ideal constant cross-section with laminar, transition-free flow.

3) A quartz capillary may be separation column and cell at the same time in this manner. There is no downward limit of the threshold volume.

Further significant benefits of this modification of the invention will be described with reference to specific applications subsequent to the following statements concerning the configuration of the capillary cell.

By way of the invention it is attempted to achieve a low-reflection transition between the sample liquid and the material of the sample cell tube.

According to a modification of the microcell system of the present invention, a metal layer is applied at least on partial sections of the outer surface of the cell tube. However, the material of the cell tube is preferably selected such that total reflection with respect to a gas, preferably air, surrounding the cell occurs at the outside thereof, since reflectivity of the metal layer is about 20% lower than in the case of total reflection. For radiation of a wavelength in the range of about 200 to 1000 nm, which is particularly significant in spectroscopic processes, the use of a quartz cell tube is to be recommended.

Unclad quartz fibers with air as the adjoining layer permit an aperture angle of 90°, i.e. an inclination of rays of up to 45° with respect to the axis.

By using unclad, i.e. "bare", capillaries as cells, the microcell systems according to the invention can be manufactured easily and at low cost.

When using the cell system according to the invention it also has to be considered that contamination and damping or tarnishing, i.e. by condensation water, condensed solvents, etc., of the surface causing total reflection should be avoided, since it adversely affects the efficiency of energy transfer. Transfer capability only breaks down, however, when the tarnish reaches a thickness of about 0.5 to 1 μm. Under laboratory conditions which can be regarded as standard to some extent, such massive tarnishing hardly ever occurs, however; if such defects do occur, they can be easily repaired by cleaning the light guides in an ultrasonic bath.

In spite of said limitations, unclad quartz light guides are a preferred material to be used in optical systems according to present knowledge, as there are only few materials which are constantly non-absorbing, isotropic and chemically inert in the UV, VIS, NIR spectral ranges of about 200 nm to 3000 nm that are important for optical analysis techniques. There is no glass covering the entire spectral range; above all, there exists no type of glass suited for the short-wave UV spectrum. Some of the extraordinarily transparent fluorides (lithium, calcium, magnesium and barium fluorides) are not isotropic ($MgF_2$), are mechanically rather soft, and sometimes cannot be processed into fibers. Besides, they are not sufficiently chemically resistant for all applications. Among the oxides, two are particularly interesting for the purpose concerned: $Al_2O_3$ and $SiO_2$, i.e. synthetic sapphire and synthetic quartz. Both materials are of extraordinary optical transparence, chemically inert and highly temperature-resistant. As regards the refractive indexes, however, they differ widely from each other. Quartz is in the lower, sapphire in the upper threshold range of optical materials.

Since, in order to realize the microcell system in a manner as simple as possible, a transition between liquid and sheath or coating material of as little reflection as possible is desired, along with preferably total reflection with respect to air; sapphire, which has a refractive index of about 1.8, is less suited while quartz, which has a refractive index of 1.458, is very well suited for this purpose, as the sample liquids usually lie in a refractive index range of about 1.3 to 1.5. (Plastics are considered to a lesser extent because of the absorption bands caused by their structure.)

In the majority of applications flow-through cells are required which ideally should be traversed laminarly without any change of cross-section, with the direction of flow and the optical path coinciding in the case of elongate cells. In conventional cells, the cross-section of the ray pencil is smaller than the flow cross-section, which is a precondition for non-reflecting, i.e. faultless, irradiation. Said system-inherent, incomplete utilization of volume renders the design of the inlet and outlet passages simple. In the solution according to the invention, however, the optical ray pencil cross-section is continuously larger than the flow cross-section of the sample, which results in the inlet and outlet passages having to cut into the path of rays somewhere when coaxial incidence of light in the "cell light guide" is desired.

According to a preferred embodiment of the flow-through cell, both ends of the cell tube are provided with an annular attachment piece comprising an inlet port and an outlet port opening into an inlet bore and an outlet bore of the cell tube, a metal layer being applied between the attachment piece and the outer surface of the cell. This embodiment is particularly suited for axial coupling and/or decoupling of radiation to the cell.

Particularly preferred is the oblique coupling and/or decoupling of radiation to the cell, however.

Coupling and/or decoupling is conveniently effected by means of a cone-shaped body which is preferably made of the same material as the cell tube and which comprises a groove on the cone sheath or coating, the radius of curvature of said groove ideally corresponding to the outer radius of the cell tube, and the cell tube being supported in the groove by interposition of a non-absorbing means such that in the case of radiation coupling the tip of the cone-shaped body points in the direction of the path of rays and, in the case of radiation decoupling, the tip of the cone-shaped body points in the direction opposite the path of rays. The cone-shaped body is preferably designed in a circular-cylindrical manner, the angle included by the longitudinal axis of the cone and the cone sheath preferably being smaller than, or equal to, a quarter of the maximum aperture angle of the step waveguide. In a cone-shaped body and a cell tube made of quartz, the angle included by the longitudinal axis of the cone and the cone sheath is about 15° to 22.5°, preferably about 20° to 22.5°, for optimum energy transfer.

In consideration of the small sizes concerned, it is not absolutely necessary to cut in an exactly fitting cylindrical groove because usually a simple 90° angular groove with an immersion means suffices.

When prismatic capillaries are used, which are common practice in thermometry, a partially ground plane face on the cone is sufficient, which considerably facilitates the manufacturing process.

For reasons of ease of operation, it has further proved favorable to connect the cell system to a light source and/or a measuring device by means of one of the afore-described aperture changers which comprises a coaxial, cone-shaped light guide or mirror with a light entry port and a light exit port, the larger of the ports facing the cell tube. The aperture changer is preferably made of the same material as the cell tube and optionally the cone-shaped body used for coupling and/or decoupling, the light entry port and the light exit port of the aperture changer preferably being cross-sectional openings perpendicular to the optical axis. The aperture changer is suitably inserted such that at least part of a preferably cylindrical light guide is connected before the respective smaller cross-sectional opening of the aperture changer, the cross-section of said light-guide portion in the area of contact with the aperture changer corresponding to said smaller cross-sectional opening, for coupling the aperture changer to a light source or a measuring device, the light guide being usually designed, at least between the end portions thereof, as a preferably flexible fiber-optical light wire.

The at least one light-conducting fiber of the light guide is suitably made of the same material as the cell tube and optionally the cone-shaped body and/or the aperture changer. Radiation is properly coupled to the cell system when the exit aperture of the cone-shaped body is larger than the entry aperture of the aperture changer, as it is thus guaranteed that radiation enters the cell tube at an angle of inclination sufficient for total reflection.

When the material used for cell tube, cone, aperture changer and, optionally, light guide is quartz, the angle included by the cone sheath of the aperture changer relative to its central axis is about 13° and the angle included by the cone sheath of the cone-shaped body relative to its central axis is about 20° to 22.5°. According to a preferred modification of the invention, the cone-shaped body and the associated aperture changer are preferably designed as a one-piece double cone.

As regards the transition of radiation from illumination or transport light guides to capillary (cell) light guides of the same admissible aperture, the application of aperture changers with double cones initially seems to be superfluous in principle, as the path of rays is expanded to a reduced aperture and subsequently restored. From a technical point of view, however, the application of double cones is very useful, since both light guides, i.e. the illuminating light guide and the capillary, only have diameters of very few 1/10 mm in micro-analysis. It is technically very difficult to incorporate the groove which is to provide the transition to the capillary in the end of the illuminating light guide. When double cones are used, this problem can be solved more easily. The advantage of such a system becomes even more apparent with respect to the transition from an illuminating light guide having a small aperture, e.g. 26°, to an unclad quartz capillary having a 44° aperture, where a tapered cone would have to be ground and polished in the fiber with a diameter of 0.6 mm and additionally provided with a groove.

As mentioned before, however, such transitions are required for high-aperture spectrometers, preferably simultaneous spectrometers, where optical energy utilization approximating the theoretically possible limit is made possible by a combination of quartz light guides and corresponding aperture changers. The light guides used comprise a core of synthetic molten quartz enclosed by a thin coating whose refractive index and dispersion must be smaller than those of quartz. As quartz already lies in the lower range of refractive indexes and dispersions (only a few fluorides are still lower), only very few coating materials can be used. At present, use is made of a specific plastic, which is chemically and thermally sensitive, however, and of doping the outer quartz wall predominantly with fluorine in a complex process. The doped quartz fibers have useful aperture angles of about 26°, i.e. the admissible inclination of rays with respect to the axis is about 13°. The values for the plastic-clad quartz fibers are only slightly higher.

Since unclad quartz fibers, which have a gas, particularly air, as the adjoining layer, permit an aperture angle of about 90°, i.e. an inclination of rays of about 45° with respect to the axis, the double cones have to be designed such that optimum transmission of light is effected. This means that the taper of the double cone directed towards the light guide is adjusted to the maximum aperture of 26° thereof, which corresponds to a cone angle of about 13° with respect to the axis of symmetry, while the taper of the double cone directed towards the capillary has to be adjusted to the maximum aperture of about 45° thereof, which corresponds to a cone angle of a maximum of 22.5° with respect to the axis of symmetry in the case of the preferred oblique coupling by means of the groove in the outer surface of the respective cone. In this manner, the cell walls are reliably prevented from becoming an independent light guide with only a reduced transition of radiation to the cell contents, which would happen in the case of coupling with the same low aperture as in the illumination light guide.

It has further proved useful to provide a cylindrical part between the aperture changer and the cone-shaped body, which part connects the exit surface of the aperture changer to the entrance surface of the cone-shaped body and which is preferably made of the same material as the cone-shaped body and the aperture changer.

According to a preferred embodiment, the double cones are preferably mounted via point-shaped contact faces in said cylindrical part.

According to another, particularly preferred embodiment of the invention, two cone-shaped bodies are spaced apart from each other such that the grooves thereof are in alignment with each other and turned upwards and that the cell tube is accommodated therein. Preferably, at least one of the cone-shaped bodies is mounted slidably along the cell tube for adjusting the optical path length and/or the longitudinal piece of the cell tube to be subjected to absorption measurement. This design is particularly useful when at least one of the double cones or both double cones are slidably mounted.

The invention further refers to the use of the afore-described microcell system in a spectroscopic system, preferably of the kind initially described, particularly in absorption spectrometry of preferably poorly absorbing liquids, e.g. the measuring of concentrations of aqueous nitrate solutions.

Another preferred application of the afore-described microcell system is in HPLC. In HPLC (High Pressure Liquid Chromatography or High Performance Liquid Chromatography), the invention provides completely new metrological opportunities. As the capillary cell interrupts the chromatography column neither with regard to cross-section nor functionally, any number of measuring stations which do not interfere with each other can be arranged successively in a lengthy row of columns. This is of particular interest when the various measuring stations are associated with various optical criteria.

As the distance between the coupling positions can be freely selected, the measured material in the capillary can be influenced by physical quantities without problem, e.g. by electronic, magnetic or high-frequency fields, by UV, alpha and neutron radiation, X-rays, etc. For this purpose, the microcell system is arranged in an appropriate reaction chamber. On account of the light guide connections to the actual measuring device, only simple parts are liable to contamination. In the case of UV irradiation, there naturally follows fluorescence measurement. If the decoupling aperture changer is made of an appropriate glass, the excitation radiation for the subsequent measurement of fluorescent radiation is automatically blocked. What was said with respect to fluorescence also applies to the measurement of Raman radiation. It should be pointed out once more that also in the case of these low-energy optical effects the arrangement according to the invention provides the geometrical optimum of energy transmission because the spectrometrically useful solid angle, i.e. the measuring aperture, is completely filled by the cell aperture. Hence, the microcell system according to the invention is of universal importance to optical measurement technology in the field of microanalytical procedures. It is also expected to contribute to progress in the field of micro-chemical reaction technology and reaction kinetics. For instance, it is a known step to chemically activate the inner walls of glass (quartz) capillaries, in which process very specific reactions take place after the filling step which occurs automatically due to the capillary forces. The invention permits superior measuring accuracy in this case.

The invention further provides a spectroscopic system in which at least one sample is illuminated by light from a light source and the light coming from the sample is concentrated on the entrance slit of at least one spectrometer, particularly a simultaneous spectrometer, and which is characterized in that a microcell system as described before is provided in the object space between the light source or the image thereof and the entrance slit.

The spectroscopic system advantageously uses as a lighting unit a point or quasi-point source of light which is imaged on the entry port of an aperture changer arranged between the light source and the object or that of a light guide connected therebefore by means of an aspherical mirror, preferably an ellipsoidal mirror. A suitable spectrometer is an arrangement comprising a diffraction grating and a receiving unit. The diffraction grating advantageously is a holographic concave grating, the receiver is a line of photodiodes. The mirror of the lighting unit and the concave grating of the spectrometer favorably have the same aperture.

Another possibility provided by the present invention resides in the fact that activated capillary sections preferably intended for single use are employed to form microcells.

Another advantage is to use the microcell system as radiation source for secondary radiation stimulated by primary radiation preferably supplied to the cell by way of oblique coupling. If fluorescent radiation is generated as secondary radiation, it can be measured directly by a photodetector. If the secondary radiation generated is fluorescent or Raman radiation, it might be recommendable to use the capillary cell as entrance slit of a spectrometer, preferably a simultaneous spectrometer, or to arrange it in the entrance slit, or to image it thereon.

Finally, it has to be noted that the invention, which essentially is a geometric-optical or energy-optical optimum solution, is not restricted to applications with high spectral resolution in a large spectral range but can be used with the same energy gain in simple monochromatic operation.

To sum up, the present invention provides a spectroscopic system capable of quantitatively detecting and evaluating all the physical quantities of energy optics mentioned in the beginning with a minimum of apparatus, specifically for the purpose of analysing small and very small quantities of substance, e.g. required in HPLC today. The intriguing feature of the system is that it requires only a minimum number of components and that it is energy-optimizing as well as comprehensive. "Comprehensive" means that all of the five optical quantities, frequency (wavelength)
velocity (refractive index)
amplitude (in absorption and emission)
azimuth of polarisation (rotary dispersion)
axial ratio of polarisation (ellipticity), can be measured directly and in the entire spectral range concerned (visible and ultraviolet).

The invention is further explained with reference to the accompanying drawings.

FIG. 3 is a schematic representation of a first version of a spectroscopic system according to the invention in an arrangement adapted for absorption measurement, in which a simultaneous spectrometer is used, too;

FIG. 5 is a sectional view of an area of the object space of another version of the spectroscopic system according to the invention in an arrangement adapted for absorption measurements.

FIG. 8b is a schematic representation, without the lighting unit, of a version of the spectroscopic system according to the invention in an arrangement adapted for differential-interferometric measurements for determining the dispersion of a substance;

FIG. 13 is a partial view of another embodiment of the microcell system according to the invention designed as flow-through cell with oblique radiation coupling;

Figure 19:
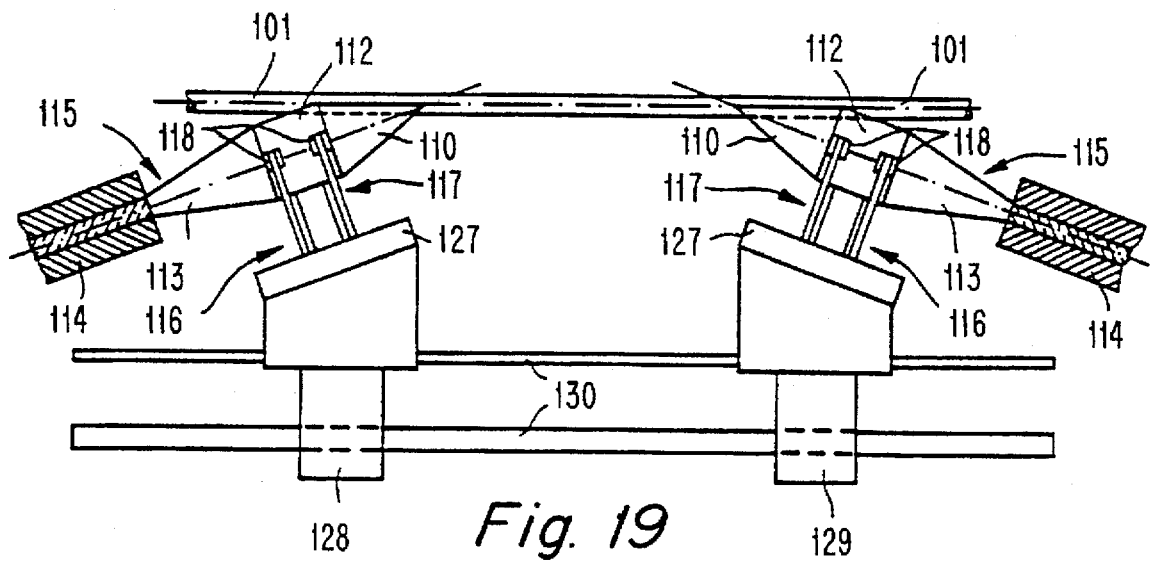
Figure 20:
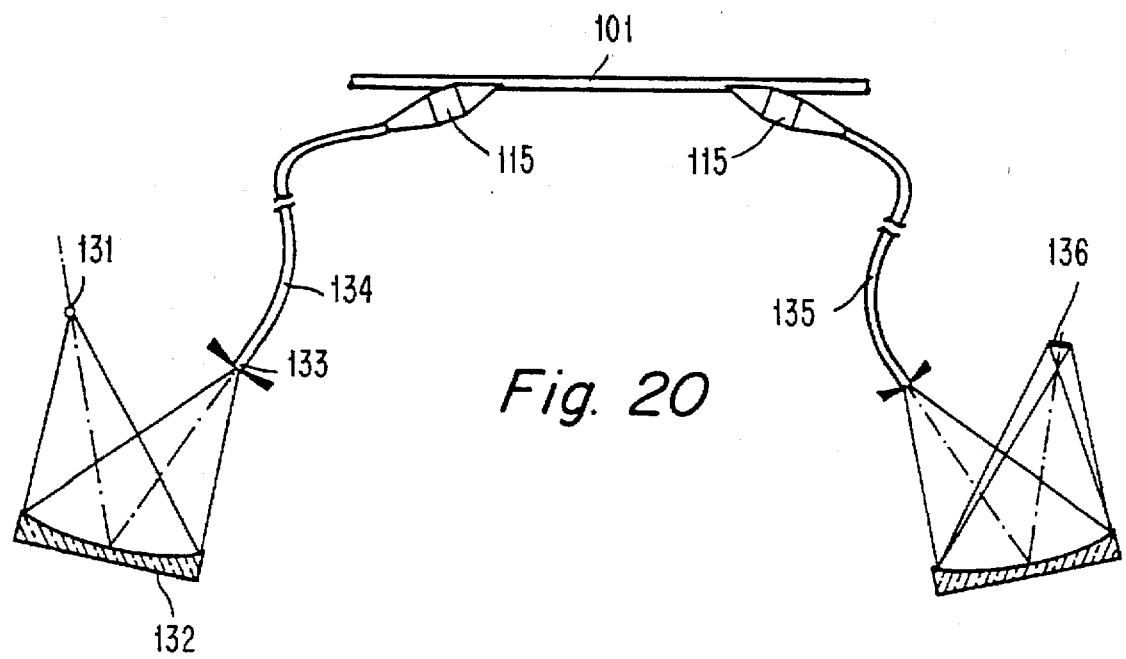
Figure 21:
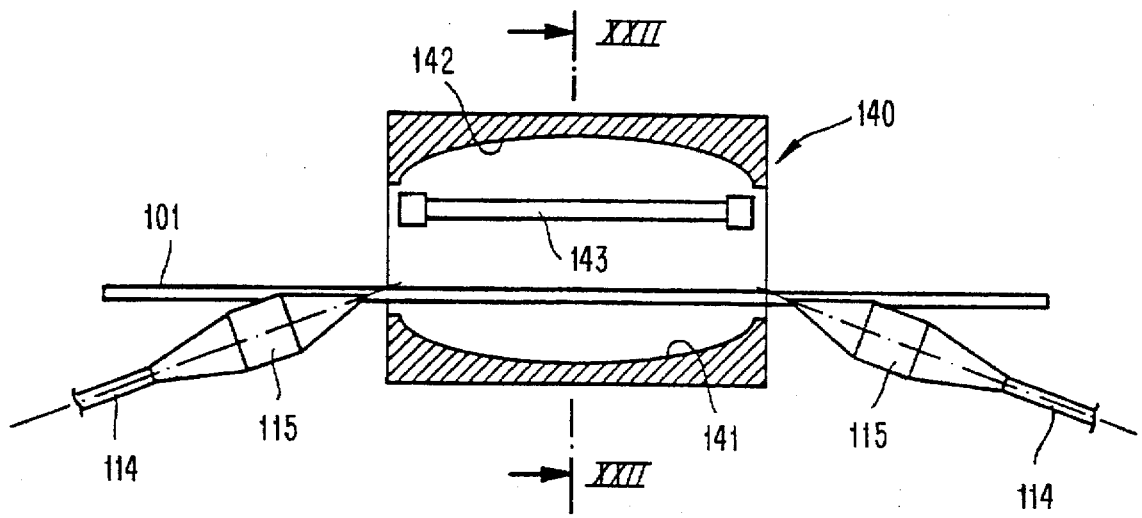
Figure 22:
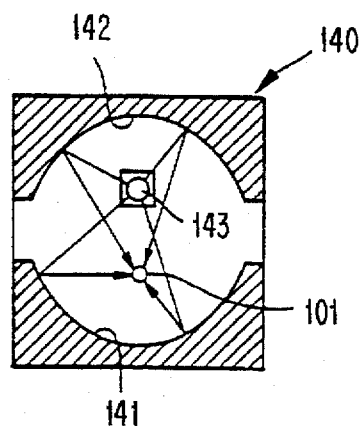
Figure 23:
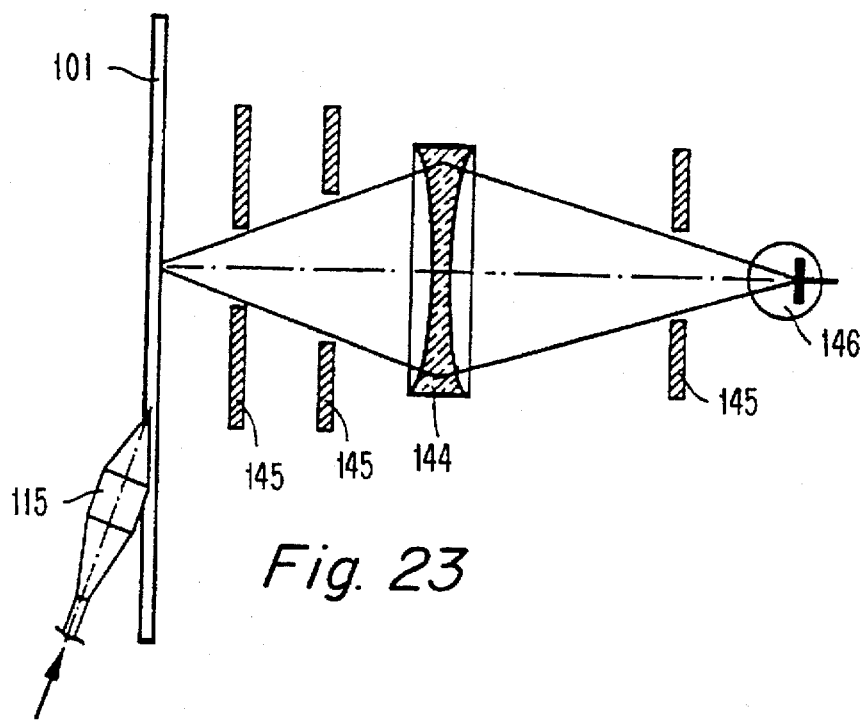
Figure 24:
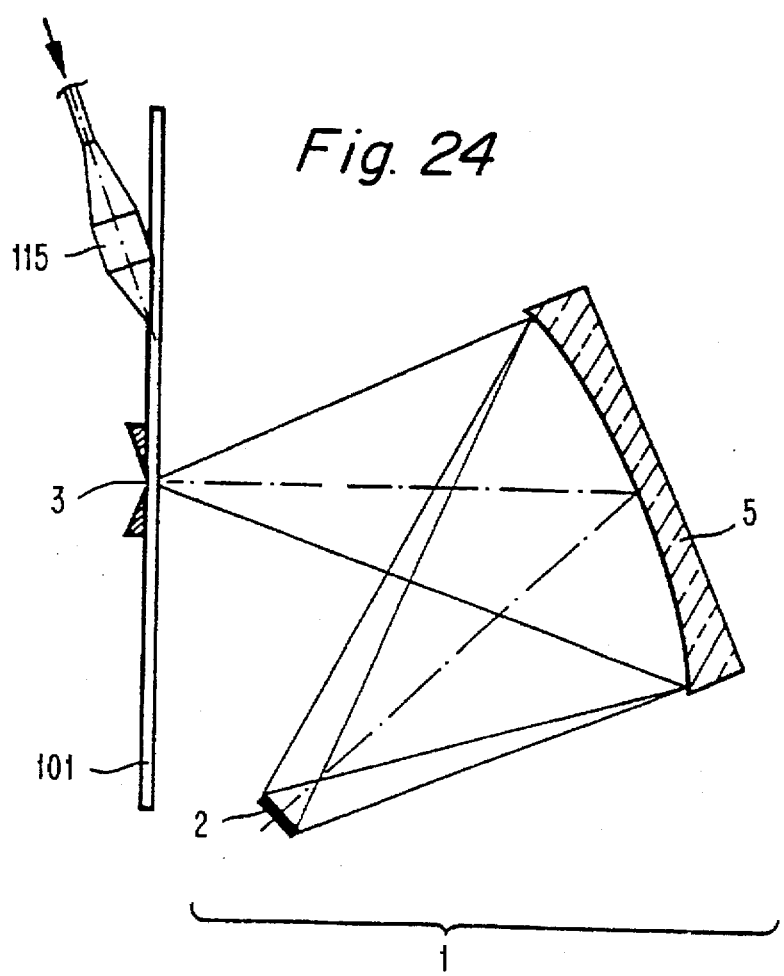

FIGS. 14a–c are sections along the IV—IV line of the microcell system shown in FIG. 13 to elucidate various possible ways of oblique radiation coupling;

FIG. 15 shows another embodiment of the microcell system according to the invention designed as a flow-through cell, wherein coupling and decoupling of radiation are effected on the basis of double cones;

FIG. 16 is a longitudinal section through the left-hand part of the arrangement shown in FIG. 15, wherein the specific cone angles suited for optimum transmission with quartz elements are indicated;

FIG. 17 is a representation corresponding to the left part of FIG. 15, comprising additional supports for the double cone;

FIG. 18 is a section along the IIX—IIX line of FIG. 17 to elucidate the support construction;

FIG. 19 is a representation corresponding to FIG. 15, wherein the double cones are displaceable along the cell tube for adjusting the optical path length;

FIG. 20 shows a spectroscopic system in which the microcell system according to the invention is used;

FIG. 21 shows the arrangement of the microcell system according to the invention in a reaction chamber;

FIG. 22 shows a cross-section through FIG. 21 along the XXII—XXII line;

FIG. 23 shows the arrangement of the microcell system according to the invention for use in integral fluorescence measurements;

FIG. 24 shows the microcell system according to the invention as a radiation source in the entrance slit of a simultaneous spectrometer, particularly for spectral measurements of fluorescent or Raman radiation.

Figure 1:
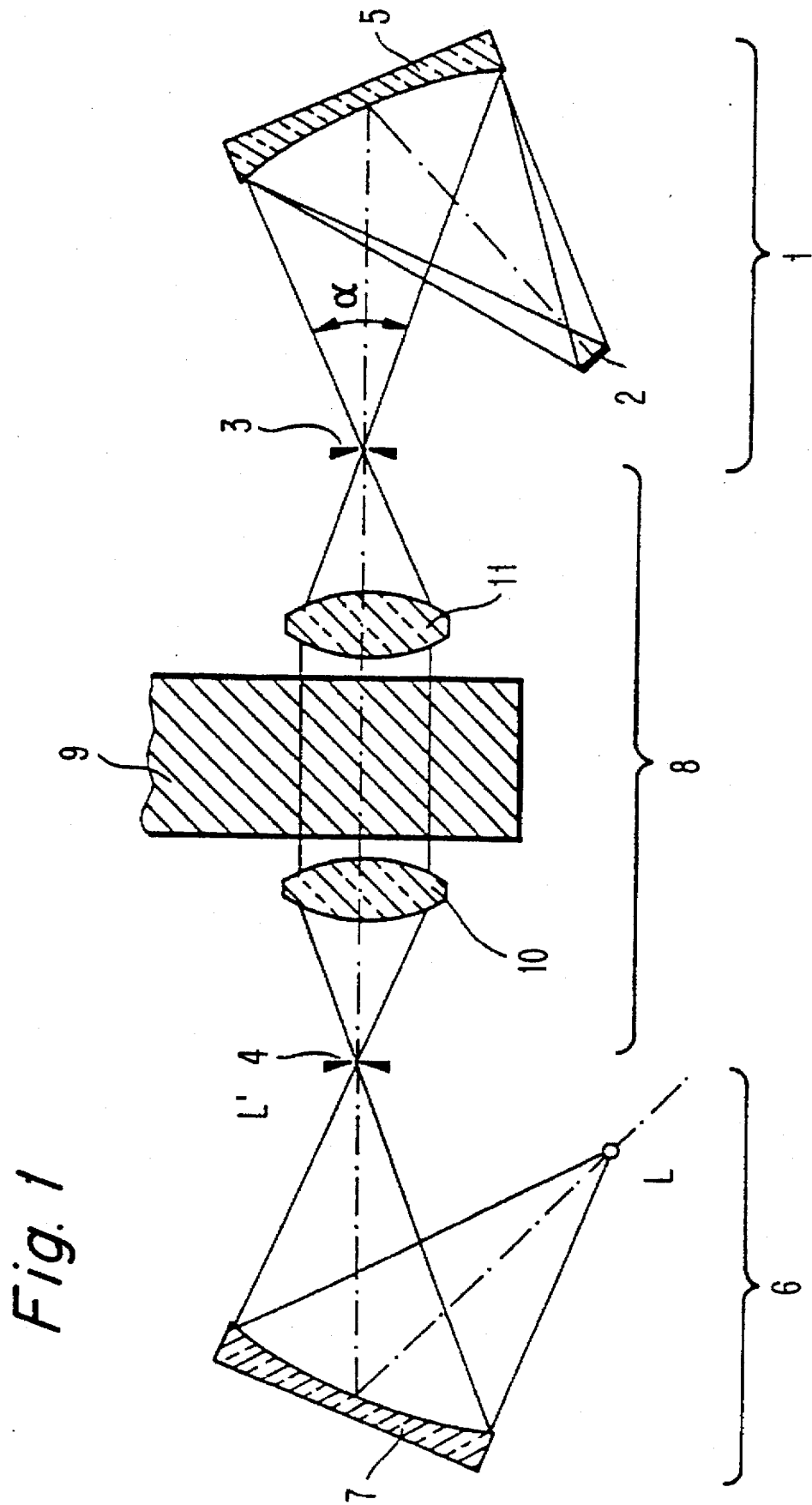
FIG. 1 is a schematic representation of a spectroscopic system according to prior art in which a simultaneous spectrometer is used.
Figure 2:
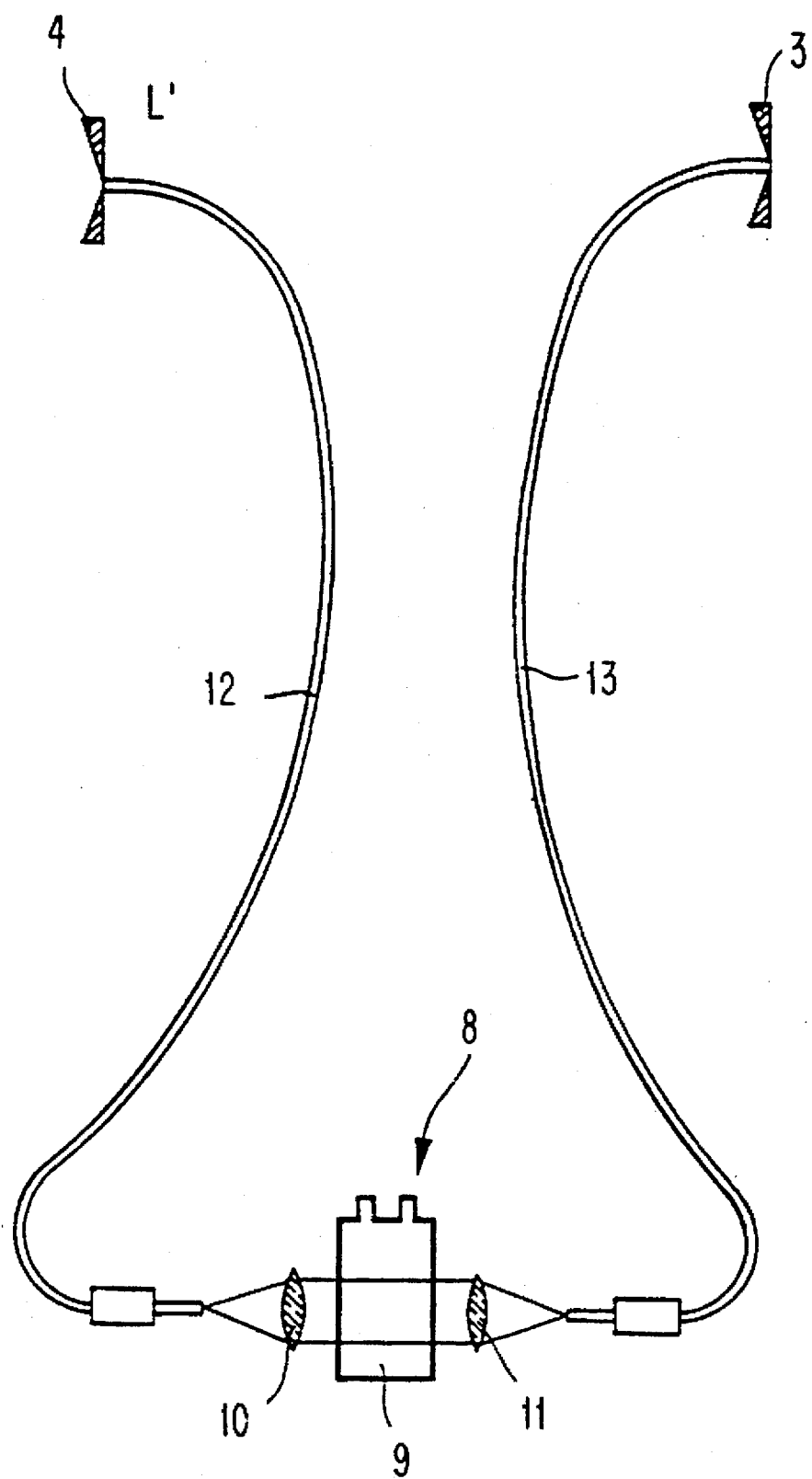
FIG. 2 shows a modification with respect to the object space of the prior art system according to FIG. 1.

The spectroscopic system according to the invention is described in the following on the basis of an example in which the basic design illustrated in FIG. 1 and described above is employed, like parts being designated by like reference numbers. The object space 8 disposed between the spectrometer 1 and the lighting unit 6 comprises a sample 9 contained in a flow-through cell. On both sides of the sample 9 there are provided aperture changers 14, 15 consisting of a coaxial cone-shaped light guide or mirror, comprising a light entry port and a light exit port and a reflecting or totally reflecting inner surface. The aperture changer 14 arranged between the image L', the light source L and the sample 9 is located with its smaller cross-sectional opening or area forming the light entry port in the plane of the image L' of the light source L, whereas the larger cross-sectional opening or area forming the light exit port may be connected to the entrance window of the cell containing the sample 9 via a piece 16 of a fiber-optical light guide. The light entry and light exit ports of the aperture changer preferably are cross-sectional openings perpendicular to the optical axis. The aperture changer 15 arranged between the sample 9 and the entrance slit 3 of the spectrometer 1 is identical to the aperture changer 14 with respect to construction and is incorporated mirror-symmetrical to the latter with respect to the sample 9 so that its light exit port formed by the smaller cross-sectional opening or area is located in the plane of the entrance slit 3 while the light entry port formed by the larger cross-sectional opening or area may be connected to the discharge opening of the cell containing the sample 9 via a piece 16 of a fiber-optical light guide.

Figure 4A:
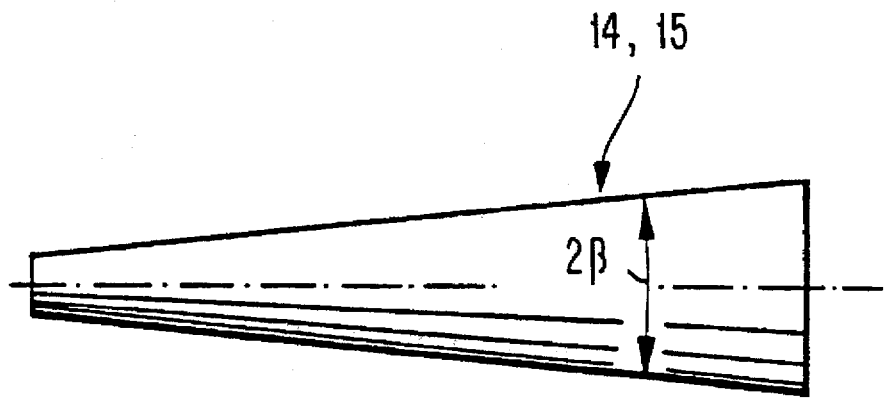
FIG. 4a is a longitudinal section of a first embodiment of an aperture changer used according to the invention.
Figure 4B:
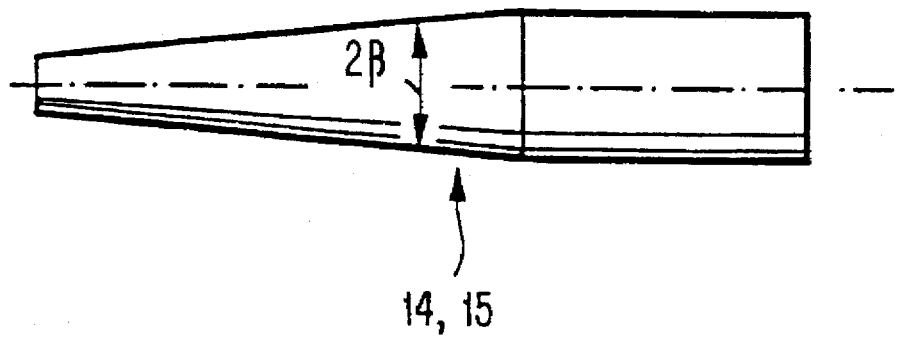
FIG. 4b is a longitudinal section of a second embodiment of an aperture changer used according to the invention, comprising a light guide connected thereto for linking the aperture changer to a sample cell.

The specific measurements and dimensions of the aperture changers 14, 15 as shown in FIGS. 4a and 4b refer to a particular embodiment of a quartz aperture changer preferred for UV spectroscopy, which will be explained in more detail on the basis of FIGS. 5a to 5d.

Figure 4C:
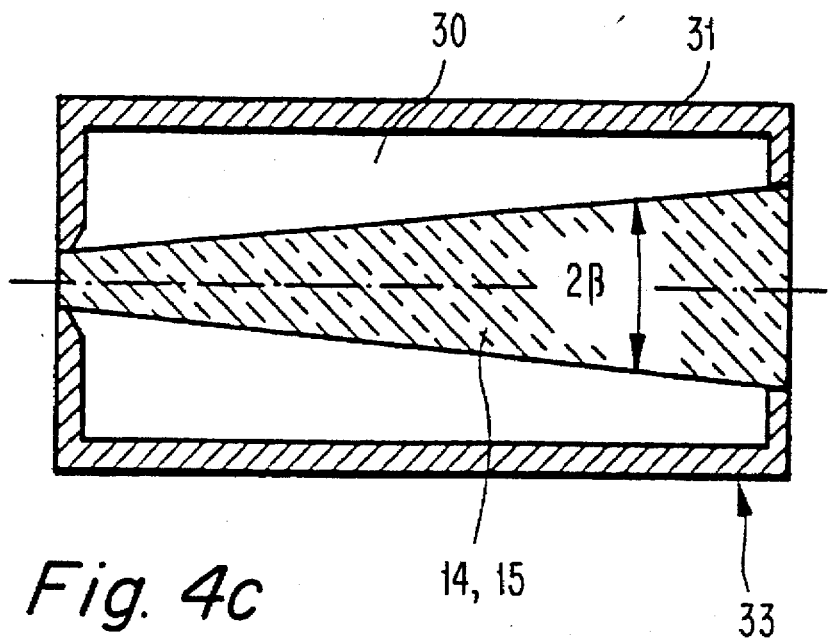
FIG. 4c shows a modification of the aperture changers illustrated in FIGS. 4a and 4b, in which the totally reflecting cone is incorporated in a hermetically sealed hollow space.

Since unprotected optical parts with internal total reflection are very contamination-sensitive, the totally reflecting cone 14 or 15 of the aperture changer is incorporated in a hermetically sealed, preferably cylindrical hollow space 30, see FIGS. 4c, d, defined by a wall 31 which suitably is made of the same material as the cone. The wall 31 is part of a mounting cylinder 33 in which the cone 14, 15 is incorporated.

Figure 4D:
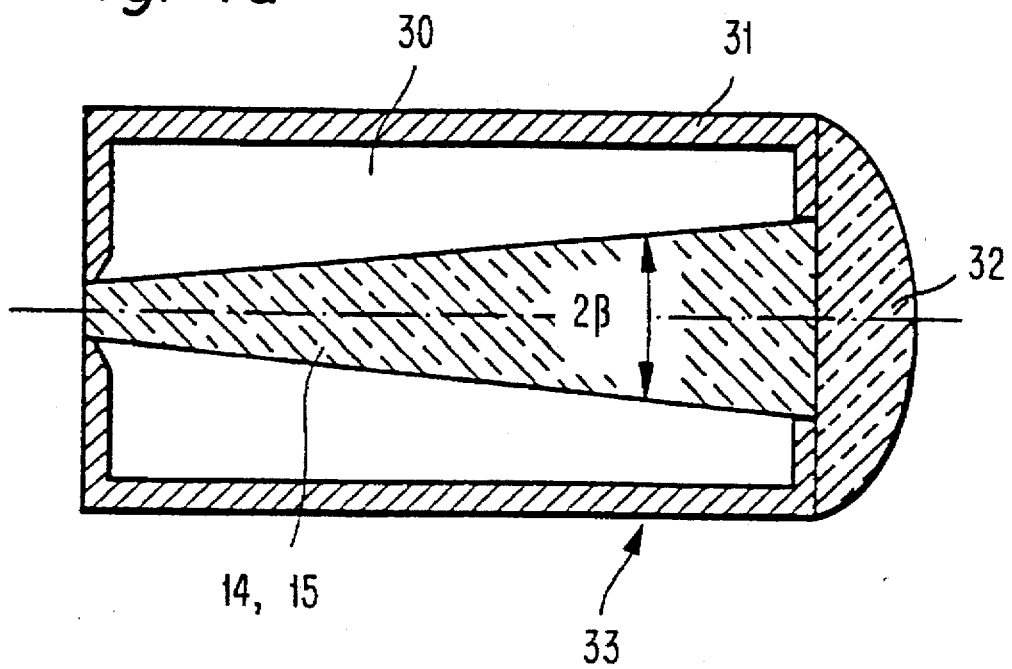
FIG. 4d shows a modification of the aperture changer of FIG. 4c comprising a correction lens.
Figure 5A:
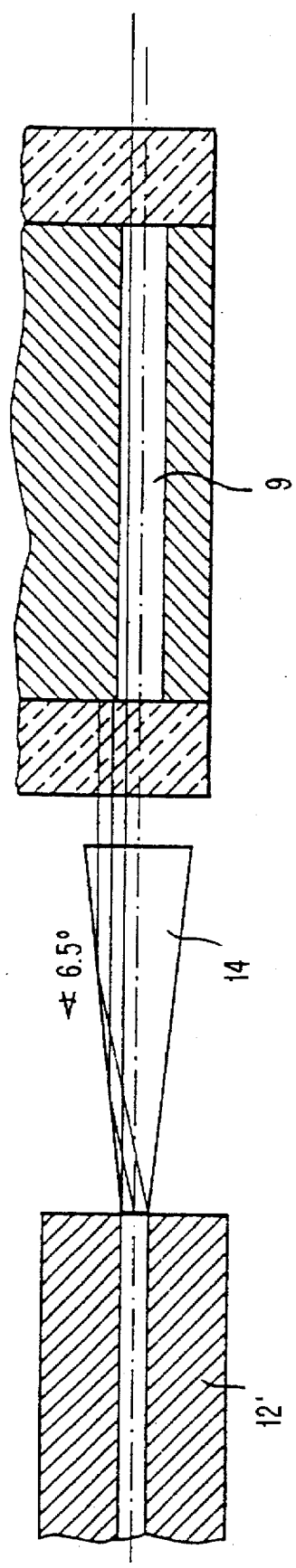
FIGS. 5a to 5d show the effects of increasingly smaller cone angles of the aperture changers.
Figure 5B:
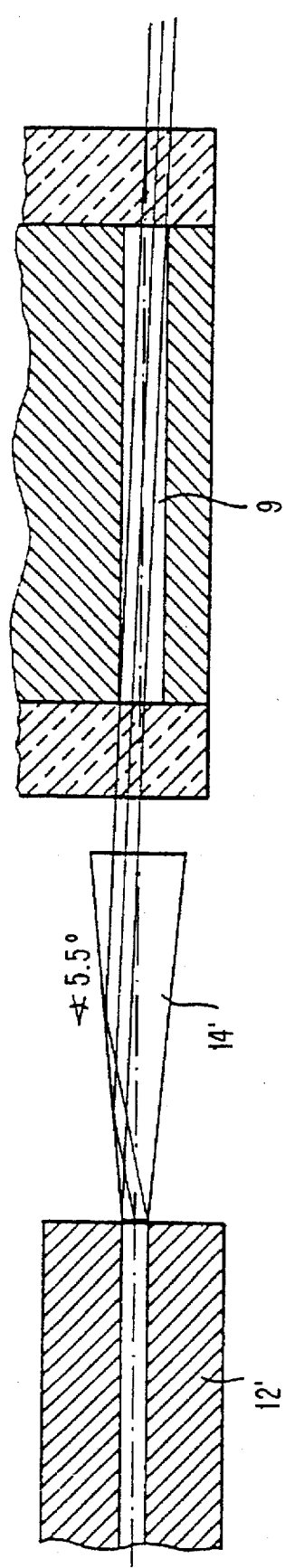
Figure 5C:
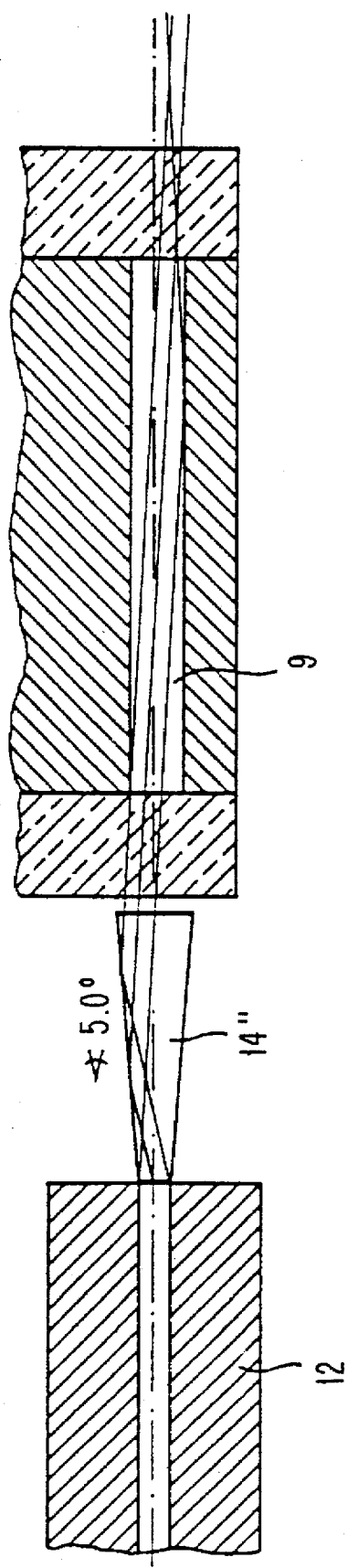
Figure 5D:
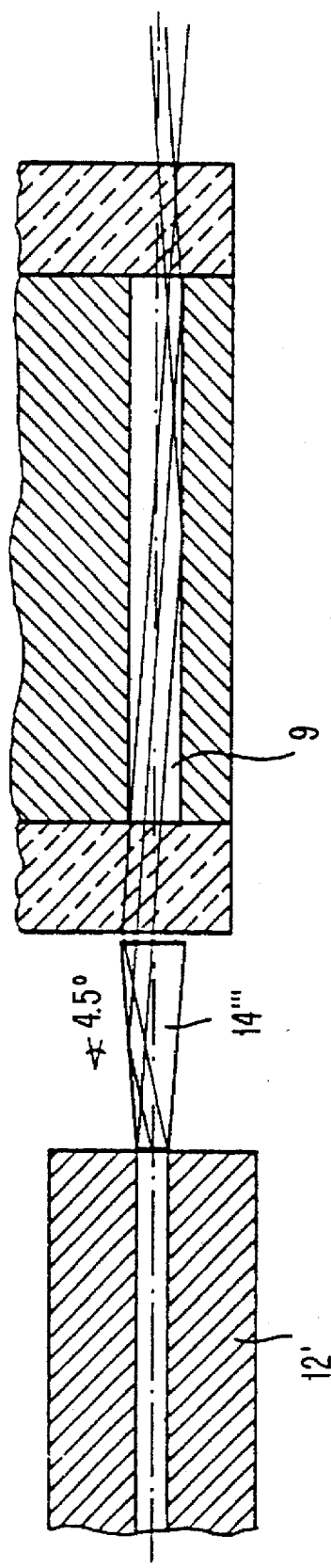

As all fiber-optical light guides, i.e. also the aperture changers 14, 15, are only capable of emitting divergent pencils of light, a correction lens 32 may be additionally attached to the aperture changer as shown in FIG. 4d in order to avoid energy loss in the marginal regions, e.g. because such stray light might be disturbing. Since the aperture is already reduced at this place, a lens can be used. In this embodiment as well as in the afore-mentioned embodiment the aperture changer is a hermetically sealed, monolithic functional unit.

The examples shown in FIGS. 5a to 5d refer to a so-called quartz-quartz fiber which transmits UV radiation particularly well and which only permits an aperture of 26° at the long-wave spectral end. This high-tech fiber is manufactured as a monofiber having a diameter of 0.6 mm.

When the aperture is $2\alpha=26°$, a half cone angle of $\beta=\alpha/2=6.5$ just equals the largest effective cross-section of the aperture changer. In micro-analytical procedures, e.g. HPLC, however, it is not the maximum but the minimum possible cross-section that is sought, and this cross-section is obtained by reducing the half cone angle $\beta$, however at the expense of a reduced effective length. The optimum results from the geometry of the given sample space which is a flow-through cell in most cases. It can be seen that the aperture changer 14' of FIG. 5b has reached an optimum with a half cone angle $\beta=5.5°$.

With respect to energy efficiency, it has to be stated that the aperture changer is the simplest mirror objective. It therefore automatically has an annular aperture or annular pupil with an optically dead zone, as shown by the section lines 17 in FIG. 3.

Referring to the afore-mentioned example, all rays with an inclination >6.5°, see FIG. 5, are reflected relative to the axis up to the limit of 13° and traverse the sample. In the core of the pencil of rays there is a small zone in which the rays traverse the sample without reflection. Therebetween is an annular zone which is lost. This fact is also shown schematically in FIG. 6.

Figure 6:
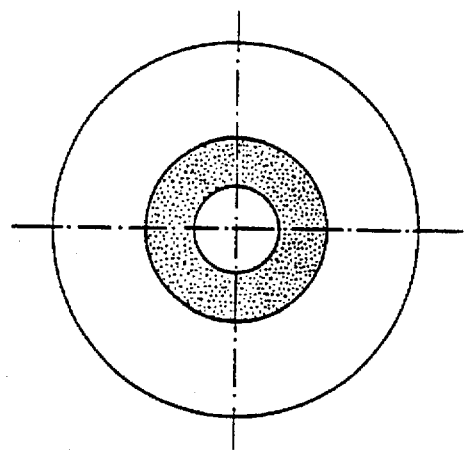
FIG. 6 is a schematic representation of the ring pupil-like effect of the aperture changer.

The closely hatched loss zone in FIG. 6 covers about 25% of the cross-section, regardless of the core zone, i.e. the degree of energy transmission of the aperture changer is at least 0.75. This degree of transmission can be increased by decreasing the half cone angle $\beta$ and adding a second reflection. This, however, increases the demands made on the manufacturer.

The cross-section ratios of light guide exit area=cell cross-section are based on the radiation law.

Since it is not the maximum but the minimum possible cell volume that is of importance in scientific analysis, as mentioned before, the following condition has to be met for complete image formation:

detector area=slit area=smaller cone opening of the aperture changer.

The detector area (e.g. Reticon S-line) is 0.0625 mm² (25 μm width and 2.5 μm height) for maximum resolution. This results in a 0.14 mm diameter of the cone apex of the aperture changer or a core diameter of about 0.15 mm of a fiber. When the aperture is ~26° as in the afore-mentioned example, the inside diameter of the cell is about 0.4 to 0.5 mm, which corresponds to a cross-section of 0.2 mm². In the case of a 10 mm-path-length cell, this means a cell filling volume of just 2 µl.

The "dead" zone of the aperture changers 14, 15 can be used for defined fixing which can be effected at the cell and/or the flexible light guide 12, 13. Being fixed to the cell, the cone end surface of the aperture changer can be used directly as a cell window. The disadvantage thereof is, however, that the aperture changers share the fate of the cell and will have to be replaced if the latter is contaminated. As a rule, the aperture changers 14, 16 will therefore be fixed to the ends of the fiber-optical light guides 12, 13. The aperture changers are then provided in a certain minimum distance before the cell windows. In order to avoid interferences, if maximum energy efficiency is of essential importance, the distance can be bridged by way of immersion.

Figure 7:
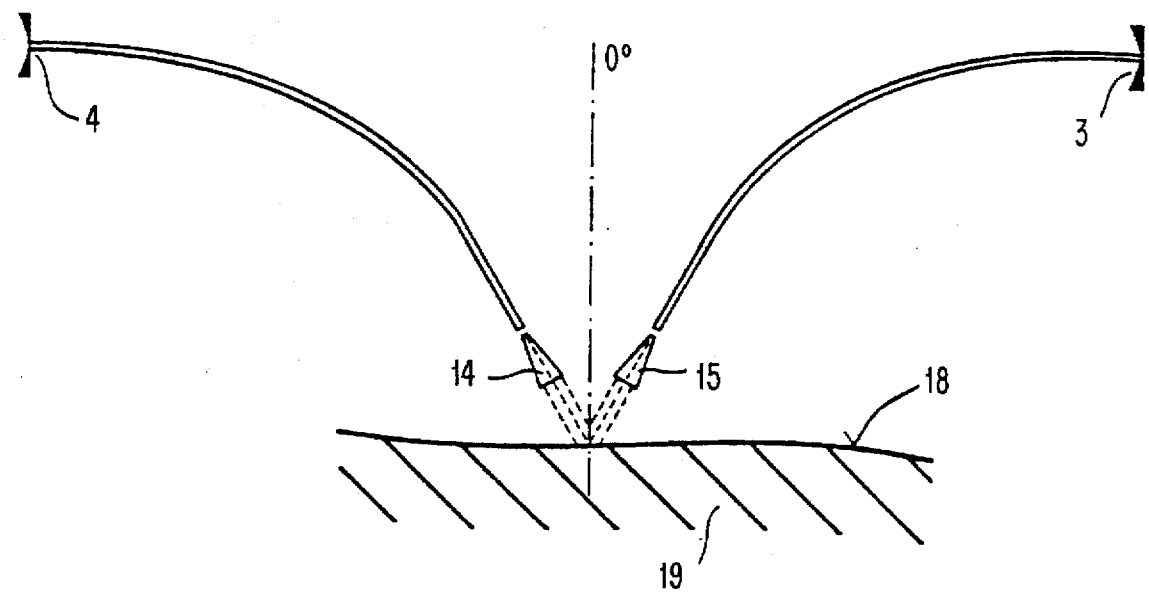
FIG. 7 is a schematic representation of the object space of another version of the spectroscopic system according to the invention in an arrangement adapted for reflection measurements with identical angles of incidence and reflection.

The embodiments described above with reference to FIGS. 3 and 5 relate to the use of the spectroscopic system according to the invention in the case of absorption measurements of samples contained in respective cells. In FIGS. 7 to 9, further preferred modifications of the spectroscopic system according to the invention are illustrated.

FIG. 7 relates to the use of the spectroscopic system according to the invention in spectral reflection or emission measurements on the surface 18 of a sample 19; this drawing only shows the object space 8, however, not the spectrometer 1 and the lighting unit 6. Although FIG. 7 illustrates reflection measurement with identical angles of incidence and reflection, the arrangement can also be modified to give a gonio-spectrophotometer having different angles of incidence and reflection.

Figure 8A:
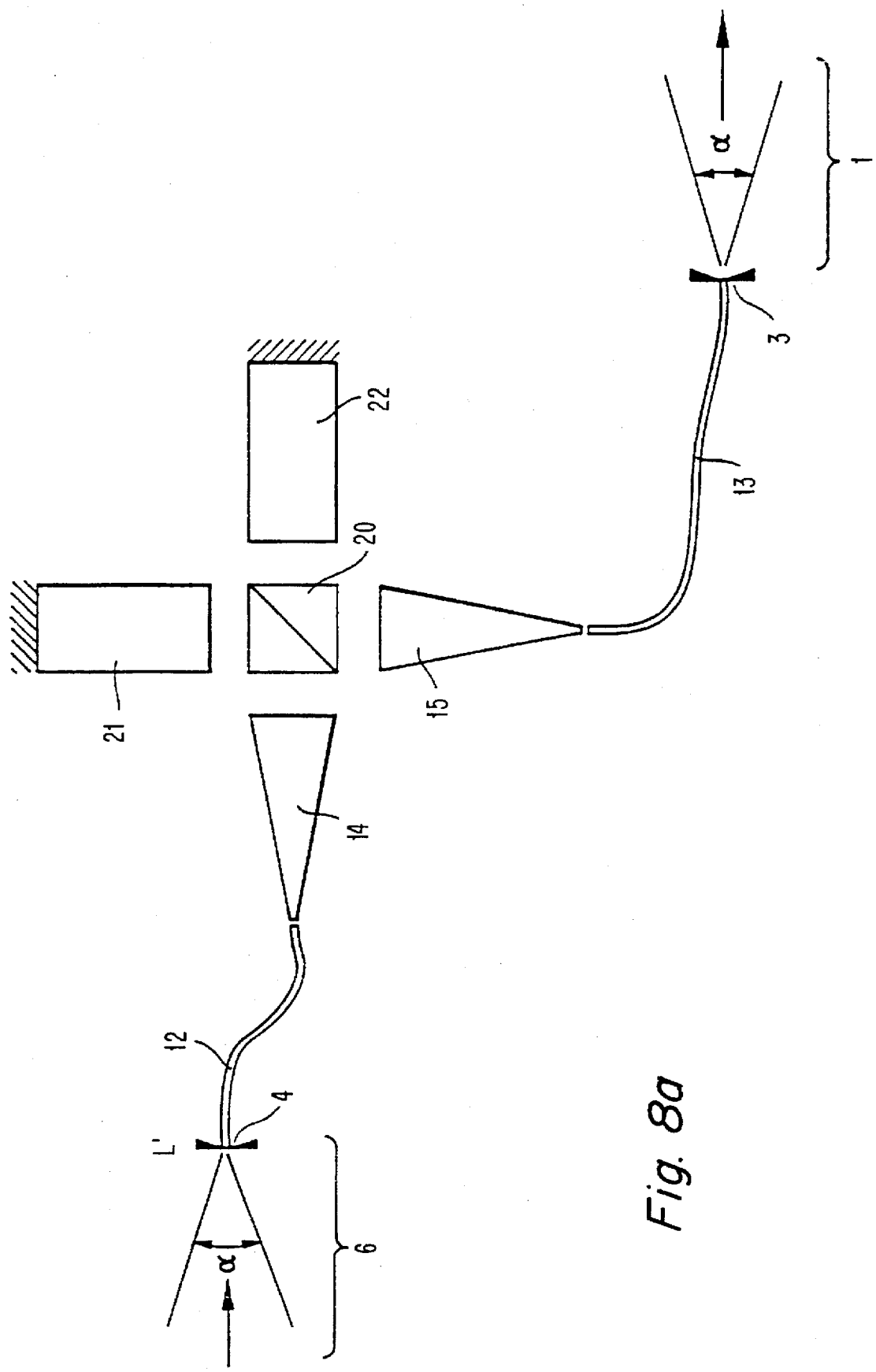
FIG. 8a is a schematic representation of the object space of another version of the spectroscopic system according to the invention in an arrangement designed as an interference refractometer for dispersion-difference measurements, the interferometer being of the Michelson type.
Figure 9:
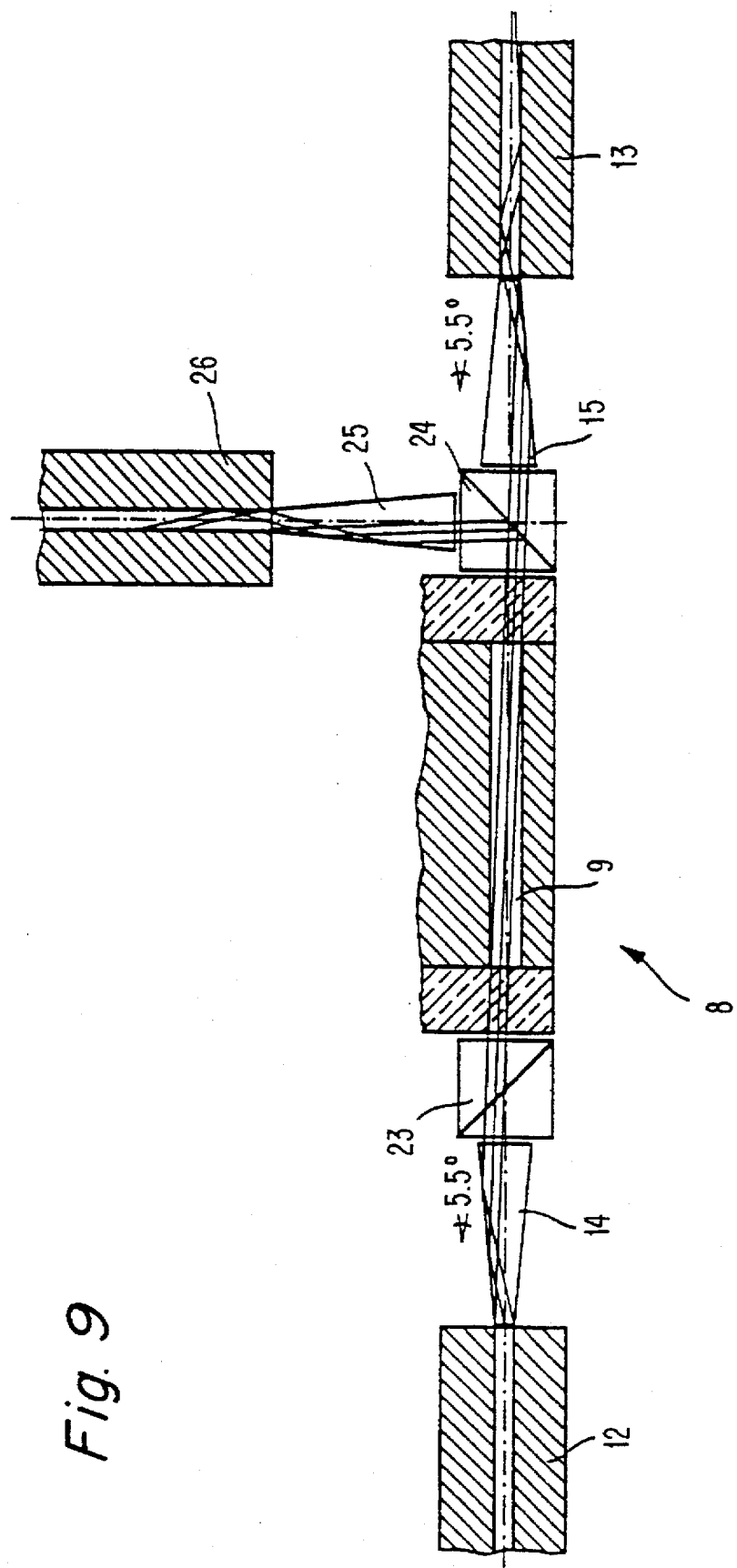
FIG. 9 is a longitudinal section of an area of the object space of another embodiment of the spectroscopic system according to the invention in an arrangement designed as a polarization spectrometer.

FIG. 8a shows the use of the spectroscopic system according to the invention as an interference refractometer for dispersion-difference measurements. The aperture changers 14 and 15 are disposed on the input side and the output side of a beam splitter 20 which receives light from the light source 6 via the light guide 12 and the aperture changer 14 and passes it on to a measuring cell 21 and a reference cell 22. The beam splitter 20 combines the rays reflected at the end of the cell 21, 22 after another passage through both cells 21, 22 and passes them to the entrance slit 3 of the spectrometer 1 via the aperture changer 15 and the light guide 13. Instead of the Michelson interferometer shown, other interferometer arrangements, e.g. of the Jamin or Mach-Zehnder type, can be used.

FIG. 8b shows another example of the application of the spectroscopic system according to the invention as an interference refractometer. The bundle of rays of preferably white light from the light source (not shown) is focussed via the inlet aperture changer 14 on a side face of a Köster prism 48 in which it is split into two bundles of rays by a semitransparent surface 49 which is preferably formed of a silver film and extends through the prism along the longitudinal plane of symmetry thereof. One bundle of rays enters a measuring cell 21, the other bundle enters a reference cell 22, said cells being fully reflecting at the ends thereof, as indicated by reference number 50. After passing through the measuring cell 21 and the reference cell 22 once more, the reflected bundles of rays re-enter the Köster prism 48 where the bundles of rays are recombined and fed to the spectrometer 1 via the outlet aperture changer 15.

As usual in interferometry, the measured quantity itself is formed of the product of optical path length and refractive index or the differences thereof. As the optical path length is the same in both partial ray traces, the result is a direct measure of the refractive index differences.

The following is a practical example of the obtainable sensitivity:

| path length in the sample | $20 \text{ mm} = 2 \times 10^{-2}$ m (double passage) |
|---|---|
| wavelength accuracy | $0.5 \text{ nm} = 5 \times 10^{-10}$ m |
| refractive index accuracy | $n - n_0 = 1 \times 10^{-8}$. |

FIG. 9 illustrates a possible way of applying the spectroscopic system according to the invention for measuring rotary dispersion. For this purpose, the system has been designed as a polarizing spectrometer; FIG. 9 only shows part of the object space 8 thereof, however. The basic designs of the spectrometer 1 with the entrance slit 3 and the lighting unit 6 with the image L' of the light source L at the location 4 correspond to the embodiment shown in FIG. 3. A polarizer 23 is provided before the cell containing the sample 9 which is followed by an analyzer 24 directing the two reference beams via the aperture changer 15 and the light guide 13 to the entrance slit 3 of the spectrometer 1 and via another aperture changer 25 and another light guide 26 connected thereto to the entrance slit of another spectrometer which is not shown in FIG. 9 but has the same design as the spectrometer 1 of FIG. 3.

On the basis of the design indicated in FIG. 9, the invention permits effective and quick measurement of rotary dispersion also in the case of small sample quantities, which is of utmost importance in biochemistry. The invention overcomes the previous difficulties, primarily related to energy, of spectropolarimetry where quick spectrum measurements or micro-methods were practically excluded because polarimetric ray traces are even more aperture-sensitive than others.

The aperture changer according to the invention provides the possibility of constructing a micro-spectropolarimeter as shown in FIG. 9. Beam path and cell correspond to those illustrated in FIG. 5. A polarizer 23, e.g. of the Glan type, having an edge length of only 3 mm can be taken from the field of laser technology without any technical modification. The analyzer 24, which also has the function of a beam splitter, is provided with the two directions of vibration thereof at an angle of +45° or −45° relative to the incident direction of vibration. The two simultaneous spectrometers coupled to the analyzer 24 via the light guides 13 and 26 with the aperture changers 15 and 25 provide a photocurrent $\Phi(x)_1$ or $\Phi(x)_2$ for each wavelength of the line of diodes 2 of the spectrometers. The investigated rotary dispersion, i.e. the course of rotation of the optical activity as spectral function is as follows:

$$\sin 2\alpha(x) = \frac{\Phi(x)_1 - \Phi(x)_2}{\Phi(x)_1 + \Phi(x)_2} .$$

It can be seen that due to the forming of ratios all spectral apparatus functions have been eliminated. What is also remarkable is the fact that the mean value of the photocurrents in the denominator of the equation exactly represents the absorption spectrum of the substance which can easily be called up via the software of an evaluation device which is not discussed in further detail in this application.

Figure 10:
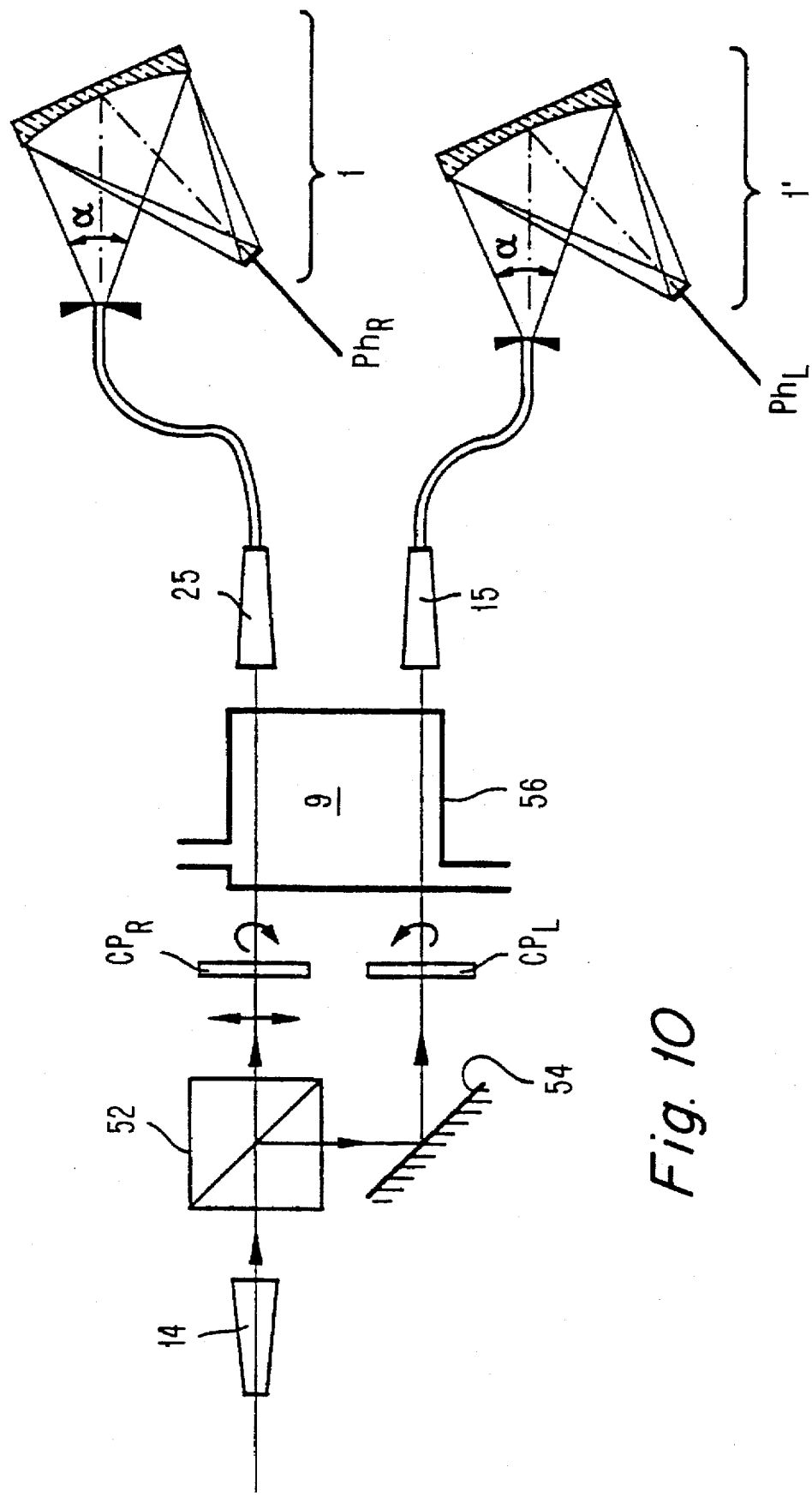
FIG. 10 is a schematic representation, without the lighting unit, of another embodiment of the spectroscopic system according to the invention in an arrangement for determining the circular dichroism.

FIG. 10 shows another possible way of using the spectroscopic system according to the invention as a device for measuring the circular dichroism (CD) which means the spectral function of the difference of absorptions for right-hand and left-hand circularly polarized light. (Fifth quantity of the field equation: axial ratio of the state of polarization). In the mathematical sense, circular dichroism is the imaginary part of optical rotary dispersion. It can be measured as absorption difference for right-hand and left-hand circularly polarized light and as refractive index difference in optical rotary dispersion. Circular dichroism only occurs in the case of anomalous rotary dispersion; with respect to its chemical structure, however, it is easier to interpret than optical rotary dispersion (just like absorption and dispersion of the linear refractive indexes). Circular dispersion spectroscopy has the disadvantage, however, that the circular dispersion spectra can only be measured simultaneously in sections due to the spectrally limited effect of the circular polarizers, i.e. the phase shift. Nevertheless, there is a demand in the art for such a device.

The embodiment of such a device as schematically illustrated in FIG. 10 comprises a beam splitter which splits the light supplied by the inlet aperture changer 14 in two ray traces which are polarized orthogonally to each other due to the use of a Glan prism 52 as beam splitter. One of said orthogonally polarized bundles of rays is subsequently directed through a left-hand circular polarizer $CP_L$ upon reflection at a mirror 54, the other is directed through a right-hand circular polarizer $CP_R$ upon linear passage through the Glan prism 52, said polarizers being phase retardation members. The bundles of rays then traverse a measuring cell 56 containing the substance to be tested. The two bundles of rays separately emerging from the measuring cell 56 are subsequently supplied to a respective spectrometer 1, 1', preferably a simultaneous spectrometer, via respective aperture changers 15, 25. As in the above-described optical rotary dispersion, the measured quantity is the difference or the sum of the photocurrents $Ph_R$ and $Ph_L$ of the two spectrometers 1, 1', the difference representing the circular dichroism, the sum representing the absorption spectrum according to the following relationships:

circular dichroism $CD=Ph_R-Ph_L$ absorption spectrum=$Ph_R+Ph_L$.

As can be seen from FIG. 10, $Ph_R$ and $Ph_L$ designate the two photocurrents. The Glan prism comprises an air gap if UV measurements are to be carried out.

In the following, the microcell system according to the invention as well as preferred applications thereof are explained in more detail on the basis of FIGS. 11 to 24.

Figure 11:
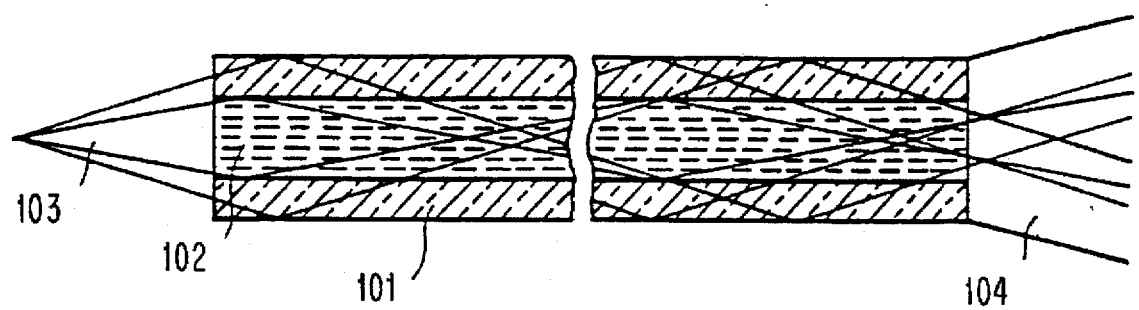
FIG. 11 is a schematic, longitudinal section of a side view of an embodiment of a microcell system according to the invention.

FIG. 11 shows a step index waveguide comprising a circular cylindrical cell tube 101 which is non-absorbing with respect to the spectral range concerned and contains in its interior a sample liquid 102. The cell tube 101 serves as sheath of the waveguide, the core of which is the sample liquid 102. The cell walls are thus integrated in the beam guiding system, as indicated by the beam path in the interior of the cell. Reference number 103 designates the entrance aperture of the cell system, reference number 104 designates the exit aperture thereof.

Figure 12:
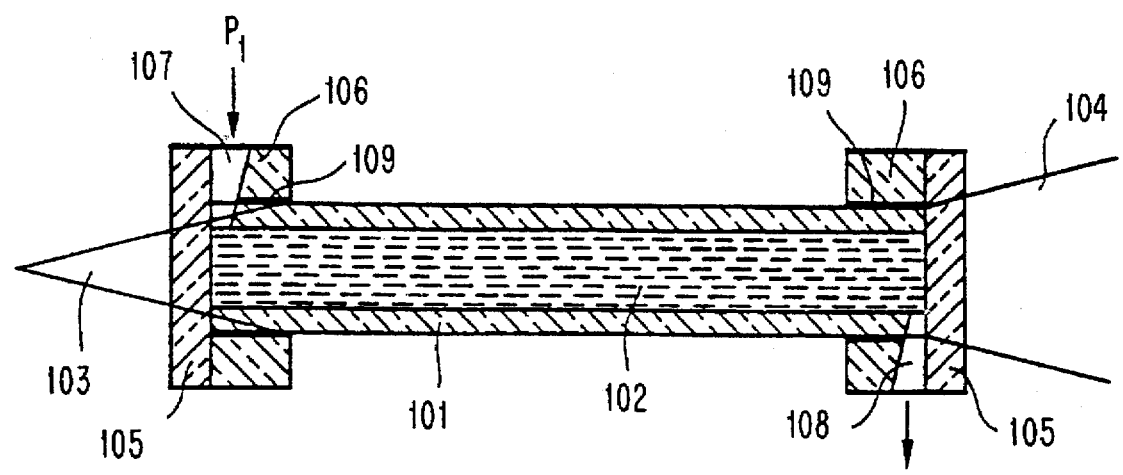
FIG. 12 is a longitudinal section of another embodiment of the microcell system according to the invention designed as a flow-through cell with axial radiation coupling.

FIG. 12 shows a possible embodiment of a flow-through cell. Reference number 101 designates the cell tube as sheath of the light guide, reference number 102 designates the sample liquid, reference numbers 103 and 104 designate the entrance and exit apertures, and reference number 105 designates the cell end windows. Annular attachment pieces 106 comprise supply bores 107 and discharge bores 108 for the sample flow which enters the cell tube 101 according to arrow $P_1$ and leaves the cell tube acording to arrow $P_2$. Said attachment pieces 106 are cemented to the end windows 105 and the cell tube 101 and strengthen the structure. In the short cylindrical section where the attachment piece 106 rests on the outer surface of the cell tube, i.e. in the region of the cement joint between 101 and 106, the outer sheath of the cell is metallically reflecting, as indicated by reference number 109, so as not to disrupt the function of light guide in this section. Reflectivity of said metal layer is lower than total reflection by about 20% but said partial loss is insignificant with respect to the total surface.

If coaxial incidence of light into the cell tube 101 of the light guide cell is relinquished, the solution concerning the passage of the sample liquid 102 is particularly simple and convincing; it can be supplied and discharged at the ends of the cell tube 101. FIGS. 13 and 14a–c illustrate the principle of such an oblique coupling of light into the circular-cylindrical cell tube 101.

While in the case of centric coupling as indicated in FIGS. 11 and 12 the theoretically existing loss rate caused by light which only propagates in the non-absorbing sheath serving as light guide is low, there is basically no such loss rate in the case of the preferred oblique coupling as indicated in FIGS. 13 and 14a–c.

In these figures, a cone-shaped body 110 consisting of the same material as the cell tube 101, e.g. quartz, is provided with a partially cylindrical or semi-cylindrical groove 111 along the cone sheath; said groove has the same radius as the outer sheath of the cell tube 101, and the cell tube 101 fits in exactly. The circular-cylindrical groove 111 may have the same depth over its entire length; however, it may also become increasingly deeper, starting from a tangential point of contact. A non-absorbing immersion means establishes the optical contact between the cone-shaped body 110 and the cell tube 101. The attached cone-shaped body 110 acts as aperture changer and thus permits optical coupling with optimum efficiency by adjusting the cone angle; in this connection, an effectively larger aperture of lighting is obtained, as indicated by the ray trace in FIG. 13, with the result that the sample liquid 102 passes through more often and the effective path length is thus increased. The basic design and the effect of such aperture changers as well as preferred applications thereof have been discussed in detail with reference to FIGS. 1 to 10.

The use of such aperture changers is based on the finding that in spectral analysis only problems regarding energy and optics (frequency, amplitude, velocity, azimuth and axial ratio of the electromagnetic radiation) have to be solved so that all questions regarding image position, image definition etc. can be deferred, and that the only important requirement is to guide the light or radiation through the object space with as little loss as possible and to adjust the inclination of rays, i.e. the apertures, to the measuring method by suitable means. As refraction and diffraction effects are subject to dispersion, i.e. they are not achromatic, means based thereon are inappropriate. The remaining means of choice therefore are reflection means; preferably, use is made of total reflection.

The cone-shaped aperture changer, which is preferably enclosed in a hermetically sealed hollow space so that the totally reflecting outer surface is protected against contamination, can also be understood as consequent reduction of a coaxial telescope with inside wall reflection.

The aperture changer can easily be coupled to the light guides which are conveniently used in many embodiments of photometric and spectroscopic systems anyway. As can be clearly seen, the cone-shaped design of the aperture changer always changes the aperture to the effect that it is large at the small cross-section of the cone and small at the large cross-section.

Hence, the aperture changer makes it possible to design photometric systems in absorption or emission on the basis of light guides of various apertures, the energy transfer of said systems being adapted to the respective optical spectrometer system of maximum efficiency.

In the modification of the cell system according to the invention as shown in FIG. 13, the discharge end of the cell tube 101 can be left open so that the sample liquid freely drops off therefrom when an integral absorption measurement is carried out; in this case, only a photo-multiplying apparatus or a corresponding measuring device is connected to the discharge end.

It is further known from the afore-said that the effect of aperture changes is reversible and variable by combining cylindrical and conical light guides. For this reason, a further cone-shaped body can be fixed to the discharge end of the cell tube, which cone-shaped body reduces the exit aperture and adjusts it to the entrance aperture of a measuring system or a light guide, for example, which supplies the emitted light to a measuring system.

This type of construction is not shown in more detail in the drawings, however.

If the opportunities provided by the aperture changers are consequently utilized, one arrives at the construction illustrated in FIG. 15. Here, the cell tube 101 containing the sample liquid 102 passed therethrough rests in the adapted grooves 111 of the cones 110. The cones 110 change into opposite cones 113 via short cylindrical parts 112, with light guides 114 being connected to the tips of said opposite cones in the above-described manner. The functional elements 110, 112, 113 are each made in one piece as double cones 115 which may be mechanically supported in the optically uncritical cylindrical part 112, as shown in more detail on the basis of FIGS. 17 and 18.

FIG. 16 represents a concrete example for coupling a quartz light guide 114 to an unclad quartz cell tube 101, as quartz light guides are particularly suited for spectroscopy in the UV and VIS spectral ranges, as mentioned before. FIG. 16 indicates the dimensions of the double cone 115 comprised of the aperture changer 113 and the cone-shaped body 110 acting as coupling member for practical application in a spectral range of about 200 to 1000 nm. Said double cone 115 with the cylindrical intermediate piece 112 establishes the connection between the doped quartz light guide 114 having an admissible aperture of about 26° and the "bare" quartz cell 101 having an aperture of about 45°. The cone 113 for the coaxial connection of the light guide 114 has an admissible total aperture angle of 26°, i.e. 13° inclincation of the cone sheath with respect to the axis. In contrast thereto, the cone arranged on the side of the cell has a total aperture angle of 40° to 45°, i.e. a 20° to 22.5° inclination of the cone sheath with respect to the axis, on account of the asymmetric incidence of light. The exact values are determined by the practical requirements. The cylindrical part 112 between the two cones primarily facilitates the manufacturing process; however, it also provides a simple and easily reproducible support as shown in FIGS. 17 and 18.

The double cone 115 which encloses half of the cell tube 101 from below via the groove 111 and which is coupled at its end remote from the cell tube 101 to the light guide 114 is supported in the region of the cylindrical part 112 by two clamps 116, 117, each of which elastically abuts the outer surface of the double cone 115 via three approximately point-shaped contact surfaces 118, 119, 120 which are offset relative to each other by 120° each. The clamps 116, 117 are tong-shaped, one jaw of the tong carrying two of the contact surfaces 119, 120, the other jaw carrying the third contact surface 118. The actuating arms 124, 125 of the clamps facing away from the jaws 121, 122 relative to the axis of rotation 123 are urged apart by a spring 126 so that the clamps can be released when the spring force is overcome. The clamps 116, 117 can be fixed to a joint support 127.

FIG. 19 illustrates a particularly interesting modification of the invention. Since the photometrically optimum path length, depending on concentration and extinction coefficient, is a function of the measuring task, and the cell may be a capillary of any length due to oblique coupling, the effective path length can be simply varied and adjusted by fixing the two double cones 115 with the clamps 116, 117 and the support 127 on respective carriages 128, 129 which are linearly and reproducibly slidable on a carriageway 130, e.g. by means of a micrometer screw (not shown). The arrangement according to the invention as illustrated in FIG. 19 is particularly suited for absorption spectroscopy on poorly absorbing liquids because the path length can be increased at will. A practical example is the direct determination of nitrate in water. The arrangement according to the invention also provides completely new metrological dimensions within the framework of HPLC (High Performance Liquid Chromatography), as already mentioned above.

FIG. 20 is a schematic representation of a simple application of the microcell system according to the invention. A continuum light source 131 with a small illuminated field is imaged through an ellipsoidal mirror 132 on the acceptance surface 133 of a transmission light guide 134. Said light guide 134 adjoins the double cone 115 according to the invention as aperture changer and coupler and provides the oblique coupling of radiation into the capillary cell 101. In a distance determined by the measuring task follows a similar double cone 115 for decoupling the radiation leading in a strictly analogous manner via a light guide 135 to the spectrometer 136 which is the actual measuring device of the arrangement. The apertures in the lighting unit and the spectrometer are preferably the same, selected to have the maximum value presently obtainable. As regards the details of the lighting unit and the spectrometer, which may be a simultaneous spectrometer, for instance, it is also referred to FIGS. 1 to 3 and the pertaining description.

In the application of the capillary cell system according to the invention, there are two crucial points with respect to spectrophotometry: first, absorption spectrometry in the nanoliter range of HPLC, e.g. corresponding to the embodiments described with reference to FIGS. 1 to 5, 9 and 10, including measurements of kinetic reaction in the submicro range, e.g. capillary electrophoresis and radiation-dependent (phototropic) effects; second, and this seems to be of particular importance, the possibility of optimum, loss-free measurement of secondary emissions, i.e. fluorescent and Raman radiation of inconceivably small quantities, wherein the flow filament may assume the function of the spectrometer slit.

Further details concerning the possible applications are referred to in the following.

Absorption spectroscopy in connection with minimum flow rates (micro HPLC) permits the spectroscopic monitoring of reactions, particularly in the field of reaction kinetics. The course of reaction in the capillary section between the coupling and decoupling positions is determined, e.g. as a function of physical and chemical influences on the sample between the coupling and decoupling positions of the capillary cell. Examples of physical influences acting on the sample between the coupling positions are as follows: optical irradiation with selected properties, such as spectral range, exposure time (e.g. flash), etc. for measuring phototropic or photolytic and photosynthetic processes; electric influence by d.c. fields and alternating fields, e.g. capillary electrophoresis; magnetic influences, e.g. Zeeman effect measurements; influence of temperature; exposure to radioactive radiation and X-rays, etc. An example of chemical influence is the use of activated capillary sections as disposable cells for specific diagnostic tasks in the field of biomedicine. In this process, the capillary sections automatically fill up on account of capillary action. Besides, the samples can be treated physically prior to or during the measurements.

An example for such an influence on reaction kinetics is schematically represented in FIGS. 21 and 22. The capillary cell system comprising the capillary tube 101 and the double cones 115 used for coupling and decoupling the radiation is guided, with the portion of the capillary tube 101 located between the coupling positions, through a reaction chamber 140 provided with ellipsoidal mirrors 141, 142. In the focal line of one ellipsoidal mirror 141, there is provided the capillary tube, in the focal line of the other ellipsoidal mirror there is provided a flash light 143. The system makes it possible to investigate photochemical processes.

In this configuration, too, the double cones having different cone angles permit the optional adjustment to two different apertures with a strictly reversible effect. The double cones can also be employed in coaxial operation in principle but show their optimum effect in the case of oblique coupling into capillaries, in which process the functions thereof as light guide are utilized. Due to the advantages of oblique coupling into very thin capillaries, light conductance is fully maintained over any length in spite of the very small cross-section. Optimum transillumination of the sample is achieved on account of central focussing at the adjusted aperture. An essential advantage of this configuration resides in the fact that the flow path need not be changed for measurement, which means that there will be no peak widenings and carry-over or delay errors. In the following, a few specific ways of coupling are stated:

a) semicylindrical groove for cylindrical capillaries (the optimum solution) according to FIG. 14a;

b) keyways for cylindrical cells, bridging of the gusset by way of immersion according to FIG. 14b;

c) partially ground plane surface for prismatic or flattened capillaries according to FIG. 14c.

The coupling process via the aperture changer cones as suggested by the invention ensures a loss-free transition and considers the different aperture conditions in the supply light guides and the measuring capillary. For in all the previously stated methods, the measured values are directly related to the incident energy which thus is the vehicle of the measured quantities sought and which is usually much larger than those. Due to the known limitation of the controllable signal-to-noise ratio, however, the detection limits of measurement are also limited when the present invention is applied.

So, no matter how useful the advance in such measurements obtained by the invention, the physically most important gain of said coupling method lies in a different field illustrated by the following two applications which are closely related. They refer to Raman and fluorescent spectroscopies. The incident primary energy is excluded from measurement not only by spectral splitting as usual but primarily by the specific guidance of rays made possible by the cell system according to the invention, as will be explained in more detail in the following.

The excitation radiation is coupled in the capillary serving as sample carrier with the cone or double cone. The aperture changer has the advantage that the sample is always optimally irradiated, no matter whether radiation is emitted from a parallel source (laser) or a point source. Due to the light guide effect, however, the excitation radiation remains confined in the capillary while the secondary light emitted under 360° leaves the capillary vertically to the axis without hindrance. The flow filament which thus is self-luminous is either imaged directly on an appropriate photo detector (diode, multiplier, or the like) for integral fluorescent measurement, as shown in FIG. 23, or it forms the entrance slit of a spectrometer, preferably a simultaneous spectrometer, for spectral emission measurement (fluorescent or Raman radiation), as indicated in FIG. 24. As it can be ensured that only the portion of flow filament is measured which corresponds to the length of the receiving diode on the diode line, a peak length in the 0.1 mm range and thus a peak volume of 1 nl and below is obtained.

In the arrangement intended for the integral measurement of fluorescent radiation emitted from the cell tube 101 as indicated in FIG. 23, the fluorescent light which is restricted by an optical system 134 and a couple of diaphragms 135 is supplied to a photo detector 136.

In the arrangement adapted for the spectral measurement of fluorescent or Raman radiation as shown in FIG. 24, the cell tube 101 is provided at the entrance slit 3 of a simultaneous spectrometer 1.

The vertical capillary tube 101 contains the traversing sample along its axis. The excitation radiation e.g. from a laser diode is coupled in the capillary via the aperture changer 115. Over a defined, short distance of 0.5 mm, for instance, the sample stimulated for secondary radiation in the capillary acts as a self-luminous slit element 3 of a spectrometer 1 which contains a holographically generated concave grating 5 and a line of diodes 2, for example, as described in detail with reference to FIGS. 1 to 3. The excitation radiation which concentrically traverses the sample in an optimum manner cannot leave the capillary due to the light guide effect while the secondary radiation, i.e. the fluorescent or Raman radiation, leaves the capillary on the side (vertically) and impinges on the grating area. Optimum energy utilization is obtained, as the luminance in the slit 3 is as high as possible and there are no loss members in the transmission path. When the internal diameter of the capillary is 0.05 mm and the utilized length is 0.5 mm, a so-called peak volume of just 1 nl is obtained, which is a value that could not be reached by any other optical method so far.

I claim:

1. Spectroscopic system for conducting micro-analytical procedures, wherein at least one sample is directionally illuminated by light emitted from a light source, and the light coming from the sample is concentrated on the entrance slit of at least one spectrometer, wherein for achromatic optical energy transfer aperture changers, an inlet aperture changer provided in an object space between the sample and light source or its image, an outlet aperture changer provided in the object space between the sample and the entrance slit, each of said aperture changers comprising a coaxial, cone-shaped member having a light entry port and a light exit port, the larger one of the ports facing the sample, the light source being a point source of light which is imaged, by means of an aspherical mirror and is transmitted to the entry port of the inlet aperture changer, the spectrometer comprising a simultaneous spectrometer whose diffraction grating is a holographic concave grating and whose receiving unit is a line of photodiodes, the sample being contained in a capillary cell arranged between the aperture changers along the optical axis such that it is irradiated in the longitudinal direction with little inclination of rays with respect to the optical axis.

2. System according to claim 1 wherein said aspherical mirror comprises an ellipsoidal mirror.

3. System according to claim 1 wherein said aspherical mirror transmits light directly to said entry port of said inlet aperture changer.

4. System according to claim 1 further including a light guide arranged to transmit light from said aspherical mirror to said entry port of said inlet aperture changer.

5. System according to claim 1 characterized in that the light entry port and the light exit port of the aperture changer are cross-sectional openings normal to the optical axis.

6. System according to claims 1, 3, 4, or 5, characterized in that a totally reflecting outer surface of each cone of each aperture changer is enclosed by a hermetically sealed hollow space whose walls are made of the same material as the cones.

7. System according to claims 1, 3, 4, or 5, characterized in that the aperture changer is provided, at the larger opening thereof, with a correction lens.

8. System according to claim 5, further including a light guide arranged to transmit light from said aspherical mirror to said entry port of said inlet aperture port, characterized in that at least a portion of the light guide is arranged opposite the smaller opening of the aperture changer, the cross-section of said light-guide portion in the area of contact with the aperture changer corresponding to said smaller opening.

9. System according to claim 8, characterized in that the light guide is formed, at least between the end portions thereof, as a flexible light wire.

10. System according to claim 5, further including a light guide arranged to transmit light from said aspherical mirror to said entry port of said inlet aperture port, characterized in that a portion of the light guide is arranged opposite the larger opening of the aperture changer, the cross-section of said light-guide portion in the area of contact with the aperture changer corresponding to said larger opening, for directly coupling the aperture changer to the sample.

11. System according to claim 8 or 10, characterized in that the portion of a cylindrical light guide arranged opposite the respective end of the aperture changer is made of the same material as the aperture changer.

12. System according to claim 4, characterized in that the light guide is in the form of a monofiber or rigid fiber rod.

13. System according to claim 9, characterized in that the light guide is in the form of an optical fiber bundle.

14. System according to claim 1, characterized in that the half cone angle B of the aperture changer is selected such that, when the object is illuminated, little inclination of rays with respect to the optical axis is achieved.

15. System according to claims 8 or 10, characterized in that the half cone angle B of the aperture changer is no greater than half of the maximum light exit angle from the light guide leading from the light source or its image to the aperture changer disposed between the light source or its image and the sample.

16. System according to claim 1 adapted for use in UV spectroscopy, characterized in that the aperture changers are quartz funnels.

17. System according to claim 16, characterized in that, when the aperture of lighting is 26°, the half cone angle of the aperture changer is no greater than 6.5°.

18. System according to claim 17, wherein said half cone angle is 5.50.

19. System according to claim 1, characterized in that the mirror of the light source and the concave grating of the spectrometer have the same aperture.

20. System according to claim 19, characterized by a 1:1 reproduction of the light source on the diodes of the photodiode line.

21. System according to claim 1, characterized in that each aperture changer has its larger opening connected to the capillary cell.

22. System according to claim 21, characterized in that said at least one cell is a flow-through cell.

23. System according to claim 1, 3, 4 or 5, for determining the dispersion of a substance dissolved in a solvent, further including a capillary cell in the form of a measuring cell containing a mixture of the substance and the solvent, a reference cell containing the solvent, and at least one beam splitter provided to supply the measuring light from the inlet aperture changer to inlets of the measuring cell and the reference cell and to supply the light reflected at an opposite end of the measuring cell and the reference cell to the outlet aperture changer.

24. System according to claim 23, wherein the measuring cell contains the solution and the reference cell contains the solvent, characterized in that a white light source is used, and that interference patterns are generated in the receiving plane of the spectrometer with the light collected in the outlet aperture changer, from which patterns the dispersion can be calculated.

25. System according to claim 24, characterized in that the beam splitter comprises a Köster prism.

26. System according to claims 1, 3, 4 or 5, characterized in that, in the direction of the illuminating beam, a polarizing device is provided upstream of the sample to be tested, and an analyzing device is provided behind the sample to be tested, for conducting polarization spectroscopy, and that a spectrometer is connected to the analyzing device via respective aperture changers for determining the rotary dispersion and the absorption spectrum of the sample on the basis of the photocurrents $\Phi(x)_1$, and $\Phi(X)_2$ from the spectrometers.

27. System according to claims 1, 3, 4 or 5, characterized in that the light emerging from the inlet aperture changer is divided into two bundles of rays by at least one beam splitter, said two bundles of rays being polarized orthogonally to each other by at least one polarizer and subsequently being subjected to circular polarization in the opposite direction by respective phase retardation members and that the circularly polarized bundles of rays are supplied, after passing through at least one measuring cell, via respective outlet aperture changers to respective spectrometers, for determining the circular dichroism and the absorption spectrum on the basis of the two photocurrents.

28. System according to claim 27, characterized in that the beam splitter comprises a Glan prism, such that the two bundles of rays emerging therefrom are orthogonally polarized to each other.

29. Spectroscopic system for conducting micro-analytical procedures, wherein at least one sample is directionally illuminated by light emitted from a light source, and the light coming from the sample is concentrated on the entrance slit of at least one spectrometer, wherein for achromatic optical energy transfer aperture changers, an inlet aperture changer provided in an object space between the sample and light source or its image, an outlet aperture changer provided in the object space between the sample and the entrance slit, each of said aperture changers comprising a coaxial, cone-shaped member having a light entry port and a light exit port, the larger one of the ports facing the sample, the light source being a point source of light which is imaged, by means of an aspherical mirror and is transmitted to the entry port of the inlet aperture changer, the spectrometer comprising a simultaneous spectrometer whose diffraction grating is a holographic concave grating and whose receiving unit is a line of photodiodes, the sample being a surface arranged between the aperture changers and whose spectral reflectivity is measured.

30. System according to claim 29, characterized in that the surface is illuminated substantially in the vertical direction.

31. System according to claim 29, characterized in that the surface is illuminated at an angle, and that the angles of incidence and reflection are the same.

32. System according to claim 29, characterized in that the surface is illuminated at an angle, the angles of incidence and reflection being different from each other.

* * * * *